US010376636B2

(12) United States Patent
Sealfon

(10) Patent No.: US 10,376,636 B2
(45) Date of Patent: Aug. 13, 2019

(54) COMPACT MECHANICAL PUMP

(71) Applicant: REPRO-MED SYSTEMS, INC., Chester, NY (US)

(72) Inventor: Andrew I Sealfon, Monroe, NY (US)

(73) Assignee: REPRO-MED SYSTEMS, INC.

( * ) Notice: Subject to any disclaimer, the term of this patent is extended or adjusted under 35 U.S.C. 154(b) by 374 days.

(21) Appl. No.: 15/126,561

(22) PCT Filed: Mar. 28, 2015

(86) PCT No.: PCT/US2015/023221
§ 371 (c)(1),
(2) Date: Sep. 15, 2016

(87) PCT Pub. No.: WO2015/149050
PCT Pub. Date: Oct. 1, 2015

(65) Prior Publication Data
US 2017/0087295 A1 Mar. 30, 2017

Related U.S. Application Data

(60) Provisional application No. 61/971,942, filed on Mar. 28, 2014.

(51) Int. Cl.
*A61M 5/24* (2006.01)
*A61M 5/145* (2006.01)
(Continued)

(52) U.S. Cl.
CPC ...... *A61M 5/1454* (2013.01); *A61M 5/14244* (2013.01); *A61M 5/24* (2013.01);
(Continued)

(58) Field of Classification Search
CPC ............ A61M 5/14244; A61M 5/1454; A61M 5/1456; A61M 5/1458; A61M 5/142;
(Continued)

(56) References Cited

U.S. PATENT DOCUMENTS 4,298,000 A * 11/1981 Thill .................... A61M 5/141
604/135
4,681,566 A * 7/1987 Fenton, Jr. .......... A61M 5/1454
128/DIG. 12

(Continued)

FOREIGN PATENT DOCUMENTS

| EP | 0289361 | 11/1997 |
|---|---|---|
| WO | WO 07/00091 | 1/1997 |

OTHER PUBLICATIONS

PCT International Search Report for International Application PCT/US2015/023221, search report dated Aug. 28, 2015 (Aug. 28, 2015).
(Continued)

*Primary Examiner* — Jason E Flick
*Assistant Examiner* — Courtney B Fredrickson
(74) *Attorney, Agent, or Firm* — Daniel W. Roberts; Law Offices of Daniel W. Roberts, LLC

(57) ABSTRACT

A compact mechanical pump is provided. The pump is adjustable between a compact form and an expanded form, where the pump can be reduced to a compact form for ease of portability and storage and to the expanded form for use as a pump.

31 Claims, 25 Drawing Sheets

(51) Int. Cl.
*A61M 5/31* (2006.01)
*A61M 5/315* (2006.01)
*A61M 5/142* (2006.01)

(52) U.S. Cl.
CPC ...... *A61M 5/3129* (2013.01); *A61M 5/31511* (2013.01); *A61M 2005/2477* (2013.01); *A61M 2005/31518* (2013.01); *A61M 2205/583* (2013.01)

(58) Field of Classification Search
CPC ...... A61M 5/24; A61M 5/178; A61M 5/2422; A61M 5/2425; A61M 5/2429; A61M 5/28; A61M 5/281; A61M 5/282; A61M 5/283; A61M 2005/31518; A61M 2005/2403; A61M 2005/2418; A61M 2005/2477
See application file for complete search history.

(56) References Cited

U.S. PATENT DOCUMENTS

| | | | |
|---|---|---|---|
| 4,737,151 A | | 4/1988 | Clement et al. |
| 5,336,201 A | * | 8/1994 | von der Decken ......................... A61M 5/1424 128/DIG. 12 |
| 5,590,654 A | * | 1/1997 | Prince .................... A61B 5/411 324/309 |
| 7,867,197 B2 | * | 1/2011 | Sims ................... A61M 5/1454 601/131 |
| 8,932,266 B2 | * | 1/2015 | Wozencroft ........ A61M 5/2033 604/198 |
| 2007/0233004 A1 | | 10/2007 | Sims et al. |
| 2011/0144584 A1 | | 6/2011 | Wozencroft |

OTHER PUBLICATIONS

Extended European Search Report for Application 15770109.5-1664 / 3122401 PCT/US2015/023221 dated Mar. 3, 2017 (Mar. 3, 2017).

* cited by examiner

COMPACT MECHANICAL PUMP

CROSS REFERENCE TO RELATED APPLICATIONS

This application claims benefit under 35 U.S.C. § 119(e) of U.S. provisional application Ser. No. 61/971,942, filed Mar. 28, 2014, the contents of which are incorporated herein by reference.

BACKGROUND

The typical therapy for primary humoral immunodeficiency is intravenous administration of immune globulin preparations, also referred to as IVIG. The IVIG is typically administered by trained personnel at a hospital or clinic, which requires patients to regularly travel to the hospital or clinic, thereby increasing not only the costs but the burden on patients receiving the therapy. Moreover, the large doses administered intravenously can trigger flu-like symptoms in many patients. Subcutaneous administration can be a better option because the immune globulin preparations can be administered weekly or biweekly in the comfort of the home, result in a more constant IgG blood level, and reduce the occurrence of the flu-like symptoms associated with bolus intravenous administration.

Despite the advantages of patient administered subcutaneous administration, many patients still receive intravenous therapy because of existing barriers to home administration. These include high cost of infusion equipment, inadequate safety, and lack of convenience of infusion systems. Many infusion pumps are large, limiting portability; require an electrical source such as an outlet or battery, limiting location and time of use; use custom syringes that may be expensive or difficult to obtain when needed; expensive to purchase and maintain; and may not be covered by insurance. Hence, there remains a need for an improved infusion pump that is lightweight, inexpensive, safe and portable and that can be used with conventional syringes.

SUMMARY

In one aspect, a pump assembly that is portable is provided. In various embodiments, the pump assembly comprises an expandable base having a proximal end and a distal end, the base comprising a first base section and a second base section, wherein the first base section is in sliding engagement with the second base section such that the first base section and the second base section are slidably movable relative to each other between a compacted position and an expanded position, wherein the base in the expanded position is adapted to seat a chamber body having a plunger, wherein the chamber body defines a bore and an outlet, and the plunger is slidably disposed within the bore; a pusher in sliding engagement with the base, wherein the pusher is dimensioned to contact the head of the plunger; a puller in sliding engagement with the base; and a spring comprising a first end portion and a second end portion, wherein the first end portion is connected to the puller and the second end portion is connected to the pusher. Slidably moving the puller distally when the chamber body having the plunger is seated in the base causes the pusher to contact and exert force on the head of the plunger, thereby causing ejection of any contents, in particular fluid contents, in the chamber. In typical embodiments, the chamber body comprises a syringe barrel, and the plunger is a syringe plunger.

In some embodiments, the pump assembly includes a cover for the base. In some embodiments, the cover is pivotally connected to the base, and the raising and lowering movement of the cover relative to the base is coupled to the movement of the puller on the base to generate the force to the head of the plunger for pumping a fluid from the chamber.

In some embodiments, the pump assembly comprises: a housing having a distal end and a proximal end, the housing comprising: an expandable base comprising a first base section and a second base section, wherein the first base section is in sliding engagement with the second base section such that the first base section and the second base section are slidably movable relative to each other between a compacted position and an expanded position, wherein the base in the expanded position is adapted to seat a chamber body having a plunger, wherein the chamber body defines a bore and an outlet, and the plunger is slidably disposed within the bore; an expandable cover comprising a first cover section and a second cover section, wherein the first cover section is in sliding engagement with the second cover section, and wherein the cover is pivotally connected to the base at a position allowing the cover to open and close, and such that slidably moving the second base section relative to the first base section moves together the second cover section relative to the first cover section when the cover is in the closed position; a pusher in sliding engagement with the base, wherein the pusher is dimensioned to contact the head of the plunger; a puller in sliding engagement with the base; a spring comprising a first end portion and a second end portion, wherein the first end portion is connected to the puller and the second end portion is connected to the pusher; and a first linkage pivotally coupled to the cover and the puller, wherein the pivots of the first linkage are located to move the puller towards the distal end when the cover is lowered and move the puller towards the proximal end when the cover is raised. Moving the puller towards the distal end by lowering the cover when the chamber body having the plunger is seated in the base causes the pusher to contact and exert force on the head of the plunger.

In various embodiments, the first linkage is rigid to translate the movement of the cover to the movement of the puller, particularly when there is resistance from the plunger disposed in the chamber body and the leverage of the cover is used to move the puller further distally. In certain embodiments, a second linkage, which can be rigid, is present and functions together with the first linkage to efficiently couple the movement of the cover to the movement of the puller.

In certain embodiments, to provide a mechanism for slidably moving the base between a compacted position and an expanded position, a base guide system disposed on the first base section or the second base section is used for guiding the first base section and second base section slidably movably between the compacted position and the expanded position. A base stop on the first base section or the second base section prevents the first base section and the second base section from separating when the first base section and the second base section are in the expanded position.

In certain embodiments, a cover guide system disposed on the first cover section or the second cover section is used for guiding the first cover section and the second cover section slidably movably between the compacted position and the expanded position. A cover stop on the first cover section or second cover section prevents the first cover section and the second cover section from separating when the first cover section and the second cover section are in the expanded position.

In some embodiments, the pump assembly further comprises a collar slidably engaged on the base for centering and/or holding the chamber body in the housing. In some embodiments, a collar stop for preventing movement of the collar distally at a defined position is used in the pump assembly.

For slidably mounting the puller, pusher, and/or the collar to the base, the pump assembly comprises one or more track systems on the base to which the puller, pusher, and collar can be slidably mounted. In certain embodiments, the track system is present on the second base section. Each of the puller, pusher, and collar can have a corresponding puller guide element, pusher guide element, and collar guide element, respectively, for slidably mounting on the one or more track systems.

In certain embodiments, the spring connected to the puller and the pusher comprises a tape spring, in particular a negator tape spring which can generate a substantially constant force on the head of the plunger when the puller is slidably moved distally, such as by lowering the cover with linkages pivotally connecting the cover to the puller.

In various embodiments, the cover is pivotally connected to the base by a hinge. The pump assembly can further comprise a damper to dampen the opening motion of the cover. In other embodiments, the pump assembly can also include one or more of: a latch assembly or lock assembly for keeping the cover in the closed position on the base; a luer locator on the distal end of the first base section for holding or locking the outlet of the chamber body on to the housing; a rejector for rejecting a non-fitting chamber body seated in the base; and a progress window for viewing the chamber body when the cover is closed.

In some embodiments, the pump assembly is used with a syringe in an infusion system for administering a therapeutic fluid. In various embodiments, the infusion system or related kits can comprise a pump assembly described herein. In various embodiments, the infusion system or related kits can include in addition to the pump assembly, one or more of: a syringe dimensioned to seat in the pump assembly; a luer connector or disc luer connector for connecting the syringe to components of the infusion system; a tubing set, in particular an infusion tubing set, such as for connecting a injection needle to the syringe; a flow controller for controlling the flow of therapeutic fluid for administration; and an injection needle set for administering the therapeutic fluid into a patient's body.

DETAILED DESCRIPTION

Figure 1:
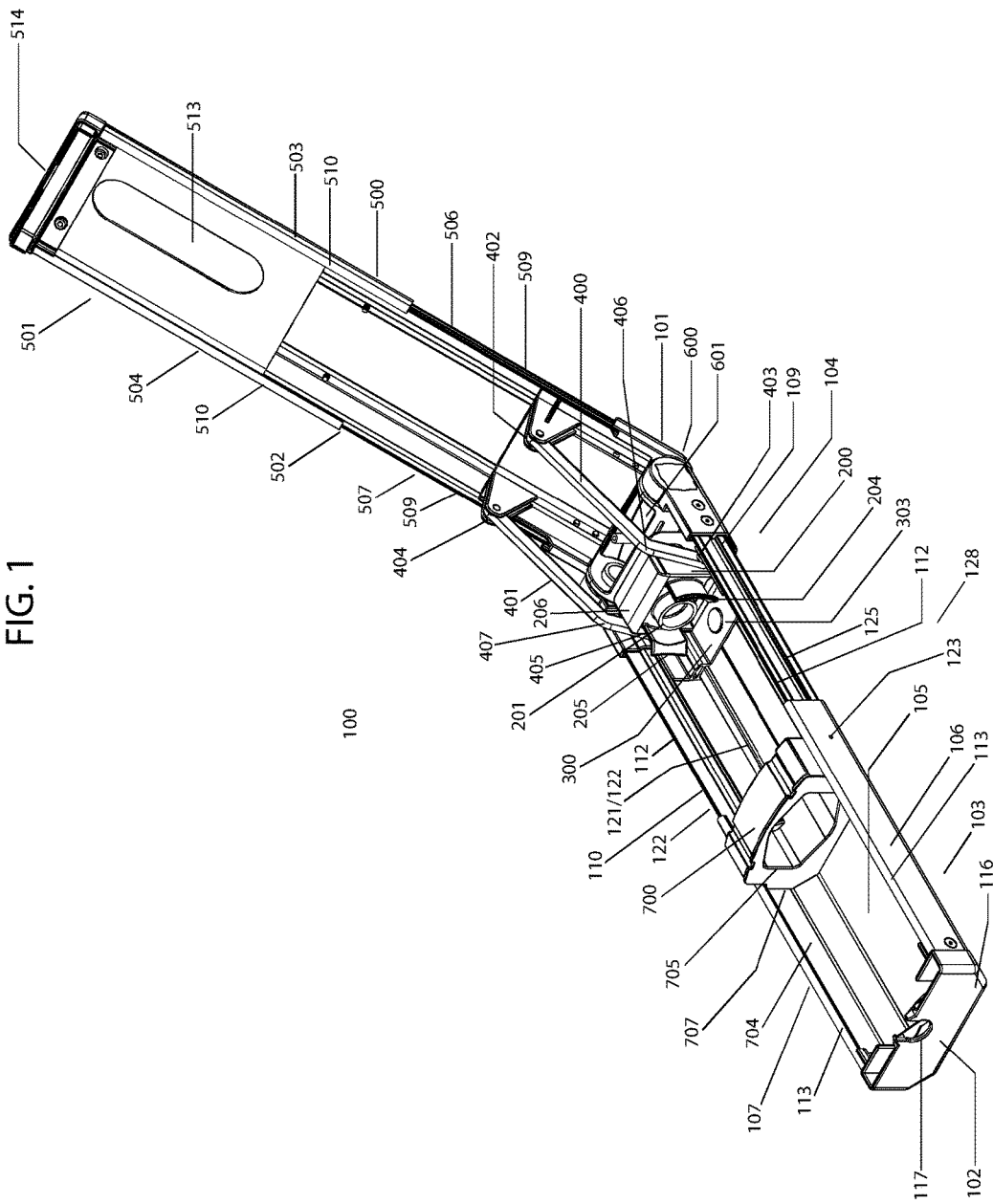
FIG. 1 is a perspective view of one embodiment of the pump assembly of the disclosure in its open telescoped state.

In one aspect, a pump assembly for dispensing liquids, e.g. therapeutic agents, is provided. In the following description, the term "longitudinal" refers to the proximal-distal axis. Also in reference to terms proximal and distal for elements which can pivot away from the base, such as a cover attached to the base, the terms proximal and distal are made in reference to the closed state of the pump assembly described herein.

In certain embodiments, the pump assembly comprises a housing having a distal end and a proximal end, the housing comprising a base and a cover, where the cover is pivotally connected to the base towards the proximal end so that the cover can be raised and lowered from the base, and the base is adapted to receive a chamber body having a plunger. The chamber body defines an outlet and a bore or lumen for receiving the plunger, and the plunger is slidingly disposed in the bore or lumen such that pushing the plunger forces out the contents of the chamber through the outlet. The chamber body has an opening at one end of the bore or lumen for receiving the plunger, where the opening can have a surface or flange, also referred to as an end piece, which extends out laterally away from the chamber body and is configured for holding the chamber body when pushing the plunger.

For providing force on the plunger, the pump assembly further comprises: a pusher, which is slidingly engaged on the base and dimensioned to contact the head of the plunger; a puller which is slidingly engaged on the base and linked to the cover such that raising the cover moves the puller proximally and lowering the cover slidingly moves the puller distally in the base; and a spring, which is connected at a first part of the spring to the puller and at a second part of the spring to the pusher such that moving the puller distally by lowering the cover causes the pusher to slidingly move distally through the connected spring, and contact and exert force on the head of the plunger when the chamber body having the plunger is seated on the base.

In certain embodiments of the pump assembly, the cover linked to the puller acts as a lever to generate force to move the puller distally and generate tension in the spring, particularly when the pusher is engaged on the head of a plunger. In certain embodiments, use of a negator spring allows generation of substantially constant force on the pusher to provide a constant pressure pump for safe administration of therapeutic fluids. A constant pressure pump generates a safe, limited constant pressure, which results in improved safety for the patient. In particular, a constant pressure pump used in an infusion system can begin and maintain the flow rate but when a restriction occurs within the patient, the resulting back-pressure in the system results in an automatic and immediate reduction in the flow rate because the infusion system with a constant pressure pump operates in an equilibrium based on the back pressure and the flow rate.

In some embodiments, the pump assembly comprises: an expandable base having a proximal end and a distal end, the base comprising: a first base section and a second base section, wherein the first base section is in sliding engagement with the second base section such that the first base section and the second base section are slidably movable relative to each other between a compacted position and an expanded position, wherein the base in the expanded position is adapted to seat a chamber body having a plunger, wherein the chamber body defines a bore and an outlet, and the plunger is slidably disposed within the bore; a pusher in sliding engagement with the base, wherein the pusher is dimensioned to contact the head of the plunger; a puller in sliding engagement with the base; and a spring comprising a first portion and a second portion, wherein the first portion is connected to the puller and the second portion is connected to the pusher, wherein slidably moving the puller distally causes the pusher to contact and exert force on the head of the plunger when the chamber body having the plunger is seated in the housing. In certain embodiments, the puller is connected to a first end portion of the spring and the puller connected to a second portion of the spring.

In certain embodiments, the pump assembly is a syringe pump assembly, where the chamber body comprises a syringe barrel and the plunger a syringe plunger, and the base in the expanded position is adapted to seat a syringe having an extended, e.g., fully extended, syringe plunger.

In certain embodiments, the puller assembly can be moved distally by various configurations of the pump assembly. For example, the puller can be manually pulled in the distal direction and a catch can be used to hold the puller in its distal position. The catch can be, for example, a hook which holds the puller in the distal position. In another embodiment, a ratchet configured into the pump assembly can be employed to move the puller distally. The pump may or may not comprise a cover.

As discussed above, in preferred embodiments, the movement of the puller slidably engaged on the base is linked to a cover attached to the base such that lowering the cover moves the puller distally, while raising the cover moves the puller proximally in the base. To provide for a pump assembly adjustable between a compacted and expanded form, the cover comprises an expandable cover which is dimensioned to cover the expandable base as the base slidably moves between the compacted and expanded positions.

In certain embodiments, the pump assembly comprises: a housing having a distal end and a proximal end, the housing comprising: (a) an expandable base comprising a first base section and a second base section, wherein the first base section is in sliding engagement with the second base section such that the first base section and the second base section are slidably movable relative to each other between a compacted position and an expanded position, wherein the base in the expanded position is adapted to seat a chamber body having a plunger, wherein the chamber body defines a bore and an outlet, and the plunger is slidably disposed within the bore; and (b) an expandable cover comprising a first cover section and a second cover section, wherein the first cover section is in sliding engagement with the second cover section, and wherein the cover is pivotally connected to the base at a position allowing the cover to open and close, and such that slidably moving the second base section relative to the first base section moves together the second cover section relative to the first cover section when the cover is in the closed position; a pusher in sliding engagement with the base, wherein the pusher is dimensioned to contact the head of the plunger; a puller in sliding engagement with the base; a spring comprising a first end portion and a second end portion, wherein the first end portion is connected to the puller and the second end portion is connected to the pusher; and a first linkage pivotally coupled to the cover and the puller, wherein the pivots of the first linkage are located to move the puller towards the distal end when the cover is lowered and move the puller towards the proximal end when the cover is raised, whereby moving the puller towards the distal end causes the pusher to contact and exert force on the head of the plunger when the chamber body having the plunger is seated in the housing.

In some embodiments, the cover can have a peripheral flange or lip for receiving the base in the closed position. In certain embodiments, the first cover section has a peripheral flange or lip adapted to receive with the first base section of the base. In some embodiments, the second cover section has a peripheral flange or lip adapted to receive the second base section of the base.

In certain embodiments, for pivotally coupling the cover to the puller, the first linkage is pivotally connected by a first pivot point hinge to the cover at a first end of the first linkage and pivotally connected by a second pivot point hinge to the puller at a second end of the first linkage. The first linkage is sufficiently rigid to efficiently translate the movement of the cover to the movement of the puller. In certain embodiments, the first linkage is bent at an angle towards the pusher on the housing. In particular, the first linkage is bent at a defined angle to form a bent-linkage. In particular embodiments, the bent angle is an obtuse angle. In some embodiments, the point of the bend in the bent linkage is offset from the center of the linkage and proximal to the puller to provide a bent linkage with at least two sections, where the first section is shorter than the second section. The first section, the shorter section, is pivotally attached to the puller while the second section, the longer section, is pivotally attached to the cover. In certain embodiments, the attachment point on the cover to the linkage is such that the linkage is within the housing when the cover is in the closed position.

In some embodiments, the syringe pump assembly further comprises a second linkage pivotally coupling the cover to the puller, wherein the pivots of the second linkage are located such that the second linkage together with the first linkage moves the puller towards the distal end when the cover is lowered and the second linkage together with the first linkage moves the puller towards the proximal end when the cover is raised. The second linkage is pivotally connected by a third pivot point hinge to the cover at a first end of the second linkage and pivotally connected by a fourth pivot point hinge to the puller at a second end of the second linkage. The second linkage is sufficiently rigid to efficiently translate the movement of the cover to the movement of the puller. In certain embodiments, the second linkage is bent at an angle towards the pusher on the housing. In particular, the second linkage is bent at a defined angle to form a bent-linkage. In some embodiments, the bent angle of the second linkage is an obtuse angle. In some embodiments, the point of the bend in the bent linkage is offset from the center of the second linkage and proximal to the puller to provide a bent linkage with at least two sections, where the first section is shorter than the second section. The first section, the shorter section, is pivotally attached to the puller while the second section, the longer section, is pivotally attached to the cover. In certain embodiments, the attachment point on the cover to the second linkage is such that the linkage is within the housing when the cover is in the closed position.

In various embodiments, to keep the movement of the first linkage and the second linkage coordinated for moving the puller, the bend angle of the first linkage is substantially same as the bend angle of the second linkage. In addition, the first linkage and the second linkage are substantially the same length, and in particular, the position of the bend is substantially the same on the first linkage and the second linkage such that the first section of the first linkage is substantially the same length as the first section of the second linkage, and the second section of the first linkage is substantially the same length as the second section of the second linkage.

To provide for parallel movement of the first linkage and the second linkage upon raising or lowering of the cover, the position or location on the cover for the pivotal attachment of the first linkage to the cover and the position on the cover for the pivotal attachment of the second linkage are at substantially equal distance from the proximal end. In addition, the position on the cover for the pivotal attachment of the first linkage from the side edge of the cover nearest the first linkage and the position on the cover for pivotal attachment of the second linkage from the side edge of the cover nearest to the second linkage are also substantially the same distance.

In some embodiments, the first linkage and the second linkage can be linear longitudinally, or alternatively, the first linkage and the second linkage can be bent along the longitudinal axis, for example to accommodate differences between the spaced apart distances for the pivotal attachment points of the first linkage and second linkage to the cover and the spaced apart distance of the pivotal attachment points of the first linkage and second linkage to the puller. In certain embodiments, the first linkage has an offset bend inward and the second linkage has a corresponding offset bend inward to accommodate a shorter spaced apart distance of the pivotal attachment points of the first linkage and second linkage to the puller as compared to the spaced apart distance of the pivotal attachment points of the first linkage and second linkage to the cover. In some embodiments, the first linkage has an offset bend outward and the second linkage has a corresponding offset bend outward to accommodate a shorter spaced apart distance of the pivotal attachment points of the first linkage and the second linkage to the cover relative to the spaced apart distance of the pivotal attachment points of the first linkage and the second linkage to the puller.

In various embodiments, the pump assembly has an expandable base, where the base comprises a first base section and a second base section, and the first base section and the second base section are in sliding engagement. In certain embodiments, the first base section comprises a first pair of opposing base sidewalls, where one wall is on one side edge of the first base section and the other wall is on the other side edge of the first base section; a distal wall on the first base section; and an open end opposite the distal wall. In various embodiments, the distal wall of the first base section has a recess, partially circular recess such as an open collar, to provide an opening for the outlet of the chamber body, and in certain embodiments, for a luer locator, as further described herein. In certain embodiments, the second base section comprises a second pair of opposing base sidewalls, where one wall is on one side edge of the second base section and the other wall is on the other side edge of the second base section; a proximal wall on the second base section, which in certain embodiments includes the hinge assembly, as further described below; and an open end opposite the proximal wall. The open end of the first base section faces the open end of the second base section when the first base section and the second base section are in sliding engagement.

In some embodiments, the first base section and the second base section are in telescoping relation to each other. By way of example and not limitation, the second base section is adapted to fit into the first base section such that the first base section and the second base section are slidingly movable relative to each other.

In various embodiments, a base guide system is disposed on the first base section or the second base section for guiding the first base section and the second base section slidably movably relative to each other between the compacted position and the expanded position. In various embodiments, the base guide system prevents the vertical separation of the first base section from the second base section when the first base section and the second base section are slidingly engaged. In certain embodiments, the base guide system also provides sufficient rigidity to withstand the vertical stresses imposed on the slidingly engaged first base section and the second base section, for example, when a chamber body having a plunger, e.g., a syringe, is seated on the base and the cover closed or lowered to apply force on the head of the plunger.

Various types of base guide systems can be implemented for the pump assembly. In some embodiments, the base guide system comprises a base guide bar or arm disposed longitudinally on the first base section or the second base section, and a corresponding complementary base guide slot on the second base section or the first base section, respectively, wherein the base guide bar or arm mates slidably into the corresponding complementary base guide slot on the second base section or first base section. In some embodiments, the base guide bar or arm is an elongated plate or stay, and the complementary base guide slot is an elongate rectangular recess dimensioned to receive the elongated plate or stay in slidable engagement. In other embodiments, the guide bar or arm is a rod, such as a cylindrical rod, and the complementary base guide slot is a bore or lumen dimensioned to receive the rod in slidable engagement.

In some embodiments, the base guide system comprises a base guide rail disposed longitudinally on the first base section or second base section, and a complementary base guide track on the second base section or first base section, respectively, wherein the base guide rail mates slidably into the corresponding complementary base guide track on the second base section or the first base section.

In some embodiments, the base guide system comprises a base guide rail having a T shaped cross section disposed longitudinally on the first base section or second base section, and a corresponding complementary base guide track comprising a base linear groove or slot having a T shaped cross sectional space on the second base section or first base section, respectively, wherein the base guide rail mates slidably into the corresponding base guide track comprising the base linear groove or slot on the second base section or first base section. In some embodiments, the base guide system comprises 2 or more base guide rails, each base guide rail having a T shaped cross section on the first base section or the second base section, and a corresponding complementary base guide track comprising 2 or more base linear groove or slots, each groove or slot having a T shaped cross sectional space on the second base section or the first base section, wherein the base guide rail mates slidably into the corresponding base guide track.

In some embodiments, the base guide system comprises a base guide rail having an L shaped cross section, and a corresponding base linear groove or slot having an L shaped cross sectional space on the second base section or first base section, respectively, wherein the base guide rail mates slidably into the corresponding complementary base linear groove or slot on the second base section or the first base section. In some embodiments, the base guide system comprises 2 or more base guide rails having L shaped cross section on the first base section or the second base section, and a corresponding complementary base guide track comprising 2 or more linear groove or slots, each groove or slot having an L shaped cross sectional space on the second base section or the first base section, wherein the base guide rail mates slidably into the corresponding base guide track.

In some embodiments, the base guide system comprises a base linear rail along the length of each side wall of the first pair of opposing side walls of the first base section or each side wall of the second pair of opposing side walls of the second base section, and a corresponding base linear track comprising a linear groove or channel, wherein the base linear rail mates slidably into the corresponding complementary linear groove or channel on the second base section or first base section. In certain embodiments, the base guide system comprises 2 or more linear rails along the length of each side wall of the first pair of side walls of the first base section or each side wall of the second pair of side walls of the second base section, and a corresponding complementary base linear track comprising 2 or more linear grooves, wherein the base linear rail mates slidably into the corresponding complementary base guide track.

In some embodiments, the base guide system comprises a base rim along the length of each side wall of the first pair of opposing side walls of the first base section or each side wall of the second pair of opposing side walls of the second base section, and a corresponding groove or channel complementary to the rim on the second base section or first base section, respectively, wherein the base rim mates slidably into a corresponding complementary groove or channel on the second base section or first base section.

In some embodiments, the base guide system comprises a base edge flange along the length of each side wall of the pair of opposing side walls of the first base section or each wall of the second pair of opposing side walls of the second base section, wherein the base edge flange mates slidably the corresponding side wall of the second pair of opposing side walls on the second base section or the side wall of the first pair of opposing side walls of the first base section. In some embodiments, the base edge flange is L shaped and mates slidably with the corresponding side wall of the second pair of opposing side walls of the second base section or the corresponding side wall of the first pair of opposing side walls of the first base section. In certain embodiments, the base edge flange curves downward to form a C, J or U shaped curl and mates slidably with the corresponding side wall of the second pair of opposing side walls of the second base section or the corresponding side wall of the first pair of opposing side walls of the first base section.

In other embodiments, the base guide system comprises a pair of side double walls on the first base section or second base section, wherein each double wall defines a space in between, and wherein each side wall of the second pair of sidewalls on the second base section or each side wall of the first pair of sidewalls on the first base section slidingly engage the corresponding double wall through the space in between the double wall.

In various embodiments, the base has a single base guide system, or in other embodiments at least two or more base guide systems. In some embodiments, the base has a first guide system and a second guide system. In some embodiments, the first base guide system is the same form of guide system as the second base guide system. In some embodiments, the first base guide system is a different form of a guide system than the second guide system.

To prevent the first base section and the second base section from separating when slidably moving from the compacted position to the expanded position, the base further comprises a base stop. In certain embodiments, the base stop is present on the first base section or the second base section for preventing the first base section and the second base section from separating when the first base section and the second base section are slidably moved from the compacted position to the expanded position. Various types of stops can be employed for this purpose. In some embodiments, the base stop can comprise a detent element on the first base section or the second base section and a corresponding counter detent element on the second base section or first base section, respectively. In various embodiments, the detent element can be a screw, protrusion, nub, or flange, and the counter detent element can comprise a complementary recess, depression, or hole which receives the detent element. In some embodiments, the counter detent element is a spring tab present in the corresponding second base section or first base section. In some embodiments, the detent element is present on the first base section or the second base section, and the counter detent element comprises a corresponding detent groove on the second base section or first base section respectively, wherein the ends of the detent groove catch the detent element to prevent the first base section and the second base section from separating.

In some embodiments, the base stop is present or integrated on the base guide system. By way of example, where the guide system comprises a base guide rod, such as a cylindrical rod and the base guide slot is a complementary bore or lumen which receives the base guide rod, the base stop can be a flange or a clamp on the end of the rod to prevent the rod from sliding off of the complementary base guide slot. In another embodiment, the detent element can be on the one or each side wall of the pair of side walls on the first base section or the second base section, and a corresponding base stop is present on the second base section or the first base section, respectively. For example, an inwardly protruding end piece is present on the end (e.g., distal or proximal end) of one or each of the side walls of the pair of side walls on the first base section or the second base section. A protruding base stop which can contact the inwardly protruding end piece is present on the second base section or first base section, respectively, for example, near the side wall with the protruding end piece. As the base is slidably moved from the compacted position to the expanded position, the inwardly protruding end piece contacts the protruding base piece and prevents the base from separating further.

In various embodiments, the pump assembly has an expandable cover, where the cover comprises a first cover section and a second cover section, and the first cover section and the second cover section are in sliding engagement. In certain embodiments, the first cover section comprises a first pair of opposing cover sidewalls, where one wall is on one side edge of the first cover section and the other wall is on the other side edge of the first cover section; a distal wall on the first cover section; and an open end opposite the distal wall. In some embodiments, the distal wall of the first cover section has a recess, a partially circular recess such as an open collar, which opposes a recess or open collar on the distal wall of the first base section to form the opening for the outlet of the chamber body when the cover is in the closed position. In certain embodiments, the second cover section comprises a second pair of opposing cover sidewalls, where one wall is on one side edge of the second cover section and the other wall is on the other side edge of the second cover section; a proximal wall on the second cover section, which in certain embodiments includes the hinge assembly, as further describe below; and an open end opposite the proximal wall. The open end of the first cover section faces the open end of the second cover section when the first cover section and the second cover section are in sliding engagement.

In some embodiments, the first cover section and the second cover section are in telescoping relation to each other. By way of example and not limitation, the second cover section is adapted to fit into the first cover section such that the first cover section and the second cover section are slidingly movable relative to each other.

In various embodiments, a cover guide system is disposed on the first cover section or the second cover section for guiding the first cover section and the second cover section slidably movably between the compacted position and the expanded position. In various embodiments, the cover guide system prevents the vertical separation of the first cover section from the second cover section when the first cover section and the second cover section are in sliding engagement. In certain embodiments, the cover guide system also provides sufficient rigidity to withstand the vertical stresses imposed on the slidingly engaged first cover section and the second cover section, for example, when the cover is lowered to move the puller distally and apply force to the head of a plunger on a chamber body, e.g., a syringe seated on the base.

Various types of guide systems described for the base guide system can also be adapted for use as the cover guide system. Accordingly, in some embodiments, the cover guide system comprises a cover guide bar or arm disposed longitudinally on the first cover section or the second cover section, and a corresponding complementary cover guide slot on the second cover section or the first cover section, respectively, wherein the cover guide bar or arm mates slidably into the corresponding complementary cover guide slot on the second cover section or first cover section. In some embodiments, the cover guide bar or arm is an elongated plate or stay, and the complementary cover guide slot is an elongate rectangular recess dimensioned to receive the elongated plate or stay in sliding engagement. In other embodiments, the guide bar or arm is a rod, such as a cylindrical rod, and the complementary cover guide slot is a bore or lumen dimensioned to receive the rod in sliding engagement.

In some embodiments, the cover guide system comprises a cover guide rail disposed longitudinally on the first cover section or second cover section, and a complementary cover guide track on the second cover section or first cover section, respectively, wherein the cover guide rail mates slidably into the corresponding complementary cover guide track on the second cover section or the first cover section.

In some embodiments, the cover guide system comprises a cover guide rail having a T shaped cross section disposed longitudinally on the first cover section or second cover section, and a corresponding complementary cover guide track comprising a cover linear groove or slot having a T shaped cross sectional space on the second cover section or first cover section respectively, wherein the cover guide rail mates slidably into the corresponding cover guide track comprising the cover linear groove or slot on the second cover section or first cover section. In some embodiments, the cover guide system comprises 2 or more cover guide rails, each cover guide rail having T shaped cross section on the first cover section or the second cover section, and a corresponding complementary cover guide track comprising 2 or more cover linear groove or slots, each groove or slot having a T shaped cross sectional space on the second cover section or the first cover section, wherein the cover guide rail mates slidably into the corresponding cover guide track.

In some embodiments, the cover guide system comprises a cover guide rail having an L shaped cross section disposed longitudinally on the first cover section or the second cover section, and a corresponding cover linear groove or slot having an L shaped cross sectional space on the second cover section or first cover section, respectively, wherein the cover guide rail mates slidably into the corresponding complementary cover linear groove or slot on the second cover section or the first cover section. In some embodiments, the cover guide system comprises 2 or more cover guide rails having L shaped cross section on the first cover section or the second cover section, and a corresponding complementary cover guide track comprising 2 or more linear groove or slots, each groove or slot having an L shaped cross sectional space on the second cover section or the first cover section, wherein the cover guide rail mates slidably into the corresponding cover guide track.

In some embodiments, the cover guide system comprises a cover linear rail along the length of each side wall of the first pair of opposing side walls of the first cover section or each side wall of the second pair of opposing side walls of the second cover section, and a corresponding cover linear track comprising a linear groove or channel, wherein the cover linear rail mates slidably into the corresponding complementary linear groove or channel on the second cover section or first cover section. In certain embodiments, the cover guide system comprises 2 or more linear rails along the length of each side wall of the first pair of opposing side walls of the first cover section or each side wall of the second pair of opposing side walls of the second cover section, and a corresponding complementary cover linear track comprising 2 or more linear grooves, where the cover linear rail mates slidably into the corresponding complementary cover guide track.

In some embodiments, the cover guide system comprises a cover rim along the length of each side wall of the first pair of opposing side walls of the first cover section or each side wall of the second pair of opposing side walls of the second cover section, and a corresponding groove or channel complementary to the rim on the second cover section or first cover section, respectively, wherein the cover rim mates slidably into a corresponding complementary groove or channel on the second cover section or first cover section.

In some embodiments, the cover guide system comprises a cover edge flange along the length of each side wall of the pair of opposing side walls of the first cover section or each wall of the second pair of opposing side walls of the second cover section, wherein the cover edge flange mates slidably the corresponding side wall of the second pair of opposing side walls on the second cover section or the side wall of the first pair of opposing side walls of the first cover section. In some embodiments, the cover edge flange is L shaped and mates slidably with the corresponding side wall of the second pair of side walls of the second cover section or the corresponding side wall of the first pair of side walls of the first cover section. In certain embodiments, the cover edge flange curves downward to form a C, J or U shaped curl and mates slidably with the corresponding side wall of the second pair of side walls of the second cover section or the corresponding side wall of the first pair of side walls of the first cover section.

In other embodiments, the cover guide system comprises a pair of side double walls on the first cover section or second cover section, wherein each double wall defines a space in between, and wherein each side wall of the second pair of sidewalls on the second cover section or each side wall of the first pair of sidewalls on the first cover section slidingly engages the corresponding double wall through the space in between the double wall.

In various embodiments, the cover has a single guide system, or in other embodiments at least two or more guide systems. In some embodiments, the cover has a first cover guide system and a second cover guide system. In some embodiments, the first cover guide system is the same form of guide system as the second cover guide system. In some embodiments, the first cover guide system is a different form of a guide system than the second guide system.

To prevent the first cover section and second cover section from separating when slidably moving from the compacted position to the expanded position, the cover further comprises a cover stop. In certain embodiments, the cover stop is present on the first cover section or the second cover section for preventing the first cover section and the second cover section from separating when the first cover section and the second cover section are slidably moved from the compacted position to the expanded position. Various types of stops can be employed for this purpose. In some embodiments, the cover stop can comprise a detent element on the first cover section or the second cover section and a corresponding counter detent element on the second cover section or first cover section, respectively. In various embodiments, the detent element can be a screw, protrusion, nub, or flange, and the counter detent element can comprise a complementary recess, depression, or hole which receives the detent element. In some embodiments, the counter detent element is a spring tab present in the corresponding second cover section or first cover section. In some embodiments, the detent element is present on the first cover section or the second cover section, and the counter detent element comprises a corresponding detent groove on the second cover section or first cover section respectively, wherein the ends of the detent groove catch the detent element to prevent the first cover section and the second cover section from separating.

In some embodiments, the cover stop is present or integrated on the cover guide system. By way of example, where the guide system comprises a cover guide rod, such as a cylindrical rod and the cover guide slot is a complementary bore or lumen which receives cover guide rod, the cover stop can be a flange or a clamp on the end of the rod to prevent the rod from sliding off of the complementary cover guide slot. In another embodiment, the detent element can be on the one or each side wall of the pair of side walls on the first cover section or the second cover section, and a corresponding cover stop is present on the second cover section or the first cover section, respectively. For example, an inwardly protruding end piece is present on the end (e.g., distal or proximal end) of one or each of the side walls of the pair of side walls on the first cover section or the second cover section. A protruding cover stop which can contact the inwardly protruding end piece is present on the second cover section or first cover section, respectively, near the side wall with the protruding end piece. As the cover is slidably moved from the compacted position to the expanded position, the inwardly protruding end piece contacts the protruding cover piece and prevents the cover from separating further.

In various embodiments, the cover also has a progress window for viewing the chamber body when the cover is closed. In preferred embodiments, the progress window at least allows viewing of the chamber body, for example a syringe barrel, near the outlet of the chamber body. In some embodiments, the progress window is present on the first cover section. In certain embodiments, the progress window can be sufficiently wide to see the chamber body. In some embodiments, the progress window is a slit, which allows for viewing of the amount of fluid remaining in the chamber body, such as in a syringe barrel. The progress window can be open, or in some embodiments, the progress window can comprise a transparent material, such as glass or clear plastic.

In various embodiments, the pump assembly further comprises one or more track systems on the base for slidably mounting: the puller and/or the pusher, or a collar for centering or holding the chamber body, as further described below. The track system is disposed to allow slidable movement longitudinally (i.e., proximal-distal) of the puller, pusher and collar. In some embodiments, at least one track system is present on the first base section. In certain embodiments, the at least one track system is integral with the first base section; that is the track system is part of the first base section when formed. In other embodiments, the at least one track system is mounted on the first base section; that is the track system is made separately and attached to the first base section. In some embodiments, the at least one track system is present on the first pair of opposing side walls of the first base section. In certain embodiments, at least two track systems are present on the first pair of opposing side walls of the first base section.

In some embodiments, at least one track system is present on the second base section. In some embodiments, the at least one track system is integral with the second base section. That is, the track system is part of the second base section when formed. In some embodiments, the at least one track system is mounted on the second base section; that is the track system is made separately and attached to the second base section. In some embodiments, the at least one track system is present on the second pair of opposing side walls of the second base section. In other embodiments, at least two track systems are present on the second pair of opposing side walls of the second base section.

In various embodiments, a single track system is used to slidably mount the pusher, puller and collar. In other embodiments, two different track systems are used to slidably mount the pusher, pusher and collar. In some embodiments, each of the puller, the pusher and the collar are slidably mounted on different track systems.

For slidably mounting the puller to the track system, the puller further comprises a puller guide element which slidably mounts the puller to at least one track system. For slidably mounting the pusher to the track system, the pusher further comprises a pusher guide element which slidably mounts the pusher to at least one track system. For slidably mounting the collar to the track system, the collar further comprises a collar guide element which slidably mounts the collar to at least one track system.

In various embodiments, each track system comprises one or more track guides for slidably mounting the puller, pusher and/or collar. The track guide slidably engages the puller guide element, the pusher guide element, and/or the collar guide element. As part of the track system, the track guide can be integral with the base, or mounted on the base. By way of example and not limitation, a flat rectangular plate having track guide can be attached to the floor of the first base section or the second base section. The track guides can be disposed on the surface of the plate or on the side edges of the plate. In some embodiments, track guides can be formed on the first base section or second base section, or attached to the floor of the first base section or second base section.

Various forms of track guides can be used for the track system. In some embodiments, the track guide comprises a track guide rail, wherein the puller guide element, the pusher guide element and/or the collar guide element mounts slidably on the track guide rail. In some embodiments, the track system comprises a single track guide. In other embodiments, the track system comprises two or more track guides.

In some embodiment, the track guide rail comprises a track guide bar, wherein the puller guide element, the pusher guide element and/or the collar guide element mounts slidably on the track guide bar. In an embodiment, the track guide bar is an elongated rectangular sheet or bar on the first base section or second base section. The guide element on the puller, pusher and/or collar can be a sleeve with a rectangular cross sectional space or a C shaped guide element which slidably mounts on the rectangular sheet or bar. In another embodiment, the track guide is a rod, such as a cylindrical rod on the first base section or the second base section, and the guide elements on the puller, pusher, and or collar can have a cylindrical bore which slidably mounts on the cylindrical rod.

In other embodiments, the track guide rail has a T shaped cross section, wherein the puller, puller, and/or collar guide element slidably mates complementary to the T shaped guide rail, for example a guide element with a T shaped cross sectional space or a guide element with a C shaped cross sectional space and wraps around the top of the T shape guide rail. Alternatively, the track guide can comprise a linear groove or slot with a T shaped cross sectional space, wherein the puller, pusher, and/or collar guide element has a cross sectional T shape which slidably mates into the T shaped groove or slot.

In some embodiments, the track guide rail has an L shaped cross section, wherein the puller, pusher, and/or collar guide element slidably mates complementary to the L shaped guide rail. Alternatively, the track guide can comprise a linear groove or slot with an L shaped cross sectional space, wherein the puller, pusher, and/or collar guide element has a cross sectional L shape which slidably mates into the L shaped groove or slot.

As noted above, the track system can have one track guide or multiple track guides. In certain embodiments, the track system comprises at least two track guides, e.g., a first track guide and a second track guide. In some embodiments, the first track guide comprises a first linear rail facing inward and extending longitudinally along the second base section, and the second track guide comprises a second linear rail facing inward and extending longitudinally along the second base section, wherein the second linear rail is on the opposing side and faces the first linear rail, and wherein the lower wall of the first linear rail and the floor of the second base section defines a first channel and the lower wall of the second linear rail and the floor of the second base section defines a second channel, wherein the first channel and the second channel face inward and towards each other. In various embodiments, the first linear rail is at one inside side edge of the second base section and the second linear rail is at the other inside side edge of the second base section. In such embodiments, the puller guide element, the pusher guide element, and/or the collar guide element slidably mount complementary to the first and second linear guide rails. In some embodiments, the puller guide element, the pusher guide element, and/or the collar guide element slidably mount on the first and second channels formed by the first and second linear guide rails, respectively.

In some embodiments, the first track guide comprises a first channel or first groove facing inward and extending longitudinally along the second base section, and the second track guide comprises a second channel or second groove facing inward and extending longitudinally along the second base section, wherein the first channel and second channel are parallel and face each other. In certain embodiments, the first channel is at one inside edge of the second base section and the second channel is at the other inside edge of the second base section. In other embodiments, the first channel is present on one of the side walls of the pair of opposing side walls of the second base section, and the second channel is present on the other side wall of the pair of opposing side walls of the second base section. In various embodiments, the puller guide element, the pusher guide element, and/or collar guide element slidably mount in the inward facing channels.

In some embodiments, the first track guide comprises a first flange extending longitudinally along one inside side edge of the second base section and the second track guide comprises a second flange extending longitudinally along the other inside side edge of the second base section, wherein the puller guide element, the pusher guide element, and/or collar guide element mates slidably to the first and second flanges. Various types of flanges can be used for the track system. In some embodiments, the first and second flanges form a C, J or U shaped curl inward and mates slidably with the puller guide element, the pusher guide element, and/or the collar guide element. In other embodiments, the flange is an L shape flange and mates slidably with the puller guide element, the pusher guide element, and/or the collar guide element.

As noted above, multiple track systems, using the same type of track guides or using different types of track guides can be used. In some embodiments, various types of track systems using different types of track guides can be combined to slidably engage the puller, pusher and/or collar to the base of the pump assembly. For example, multiple sets of channels disposed on the second base section, including the pair of opposing side walls of the second base section, can be adapted to slidably engage the puller, pusher and collar to the base. In a specific embodiment, the pump assembly comprises a first track system and a second track system, wherein the first track system comprises a first channel and a second channel, wherein the first channel faces inward and extends longitudinally along one inside edge of the second base section, and the second channel faces inward and extends longitudinally along the other inside edge of the second base section, wherein the first channel and second channel are parallel and face each other; and the second track system comprises a third channel and a fourth channel, wherein the third channel faces inward and extends longitudinally along the inside face of one side wall of the pair of side walls of the second base section, and the fourth channel faces inward and extends longitudinally along the inside face of the other side wall of the pair of side walls of the second base section, wherein the third channel and the fourth channel are parallel and face each other. In certain embodiments, the puller and the pusher are slidably engaged to the first track system, while the collar is slidably engaged to the second track system. In another specific embodiment, the puller and pusher are slidably engaged to the second track system, while the collar is slidably engaged to the first track system.

In another specific embodiment, the pump assembly comprises a first track system and a second track system, wherein the first track system comprises a first channel and a second channel, where the first channel faces inward and extends longitudinally along one inside edge of the second base section, and the second channel faces inward and extends longitudinally along the other inside edge of the second base section, wherein the first channel and second channel are parallel and face each other; and the second track system comprises a first linear groove or slot with an L shaped cross sectional space extending longitudinally along the inside face of one side wall of the pair of opposing side walls of the second base section, and a second linear groove or slot with an L shaped cross sectional space extending longitudinally along the inside face of the other side wall of the pair of opposing side walls of the second base section, wherein the first linear groove or slot and the second linear groove or slot face each other. In certain embodiments, the puller and the pusher are slidably engaged to the first track system, while the collar is slidably engaged to the second track system. In other embodiments, the puller and pusher are slidably engaged on the second track system, while the collar is slidably engaged on the first track system.

As will be apparent to the skilled artisan in view of the guidance provided in the present disclosure, various types of track systems, including combinations of different track systems can be used in the pump assembly.

In various embodiments of the pump assembly, the pusher is slidably engaged on the base and dimensioned to contact the head of the plunger. In various embodiments, the pusher can be any form sufficient for the purposes in the pump assembly. In some embodiments, the puller can comprise a pusher sled or plate, wherein the sled or plate slidably engages the track system through the pusher guide element, as further described herein. In some embodiments, the pusher can have wheels, rollers, or bearings, particularly micro wheels, micro rollers or micro bearings, attached to the pusher, such as to the bottom of the pusher, to reduce the friction on the pusher at is slidably moves in the base. The plunger head contacting portion of the pusher can be adapted to contact any type of plunger head, including plunger heads of different shapes and surfaces. In certain embodiments, the plunger head contacting portion can be substantially rectangular, substantially circular, substantially elliptical, substantially D, or substantially C cross sectional shape, and be solid or have a recessed space for contacting the plunger head. In some embodiments where the plunger head contacting portion comprises a recessed space, the recessed space can have internal supporting members, such as ribs or internal walls (e.g., angled or vertical). In some embodiments, the plunger head contacting portion can have a recessed space or configured in any three dimensional shape to accept the head of the plunger. While the plunger head contacting portion can be attached to the other elements of the pusher, such as the spring housing, in other embodiments, the plunger head contacting portion can be separate and be slidably engaged on the track system separately from the other portion of the pusher. In some embodiments, the pusher has a latch on the plunger head contacting portion of the pusher to latch onto the plunger head when the pusher contacts the plunger head. The latch can be engaged onto the plunger head while the chamber body having the plunger is empty by closing the cover to move the puller and the pusher distally until the pusher contacts the plunger head. By having a tubing attached to the outlet of the chamber body and connected to a reservoir of fluid, the chamber body can be filled in the pump assembly by opening and raising the cover to move the puller and pusher proximally, which withdraws the plunger from the chamber body and allows the chamber in the chamber body to fill with fluid from the fluid reservoir. In certain embodiments, the latch can be spring loaded latches that clip onto the head of the plunger when the pusher comes in contact with the plunger head.

In a further embodiment, the pusher also has a plunger head centering structure which guides the plunger head to the plunger head contacting portion of the pusher. In an embodiment, the plunger head centering structure of the pusher can comprise a conical structure, with the wider opening of the conical centering structure facing distally, towards the head of plunger. In other embodiments, the plunger centering structure comprises centering wings which curve outward from the pusher towards the distal end, thereby guiding the plunger head to the plunger head contacting portion. Other various embodiments of the plunger head centering structure will be apparent to the skilled artisan.

As discussed above, the pusher further comprises a pusher guide element, wherein the pusher guide element slidably mounts the pusher on the track system, in particular the pusher guide element mates slidably with the one or more of the track guides of the track system. In certain embodiments, the pusher guide element comprises a pusher sled or plate which mates slidably with the first track guide and the second track guide, such as channels disposed on the inside side edges of the second base section. In various embodiments, the pusher further comprises a pusher spring housing and a pusher spool, wherein the pusher spool is mounted in the pusher spring housing, and the spring, particularly a tape spring, is coiled around the pusher spool. In certain embodiments, the pusher spool comprises a drum, where the spring, in particular a tape or ribbon spring, is coiled around the drum. The drum can be mounted on a drum shaft present on the spring housing. In some embodiments, the pusher spool is a shaft, where the spring is coiled around the shaft. In certain embodiments, the spring is attached to the pusher without being coiled around a pusher spool.

In various embodiments of the pump assembly, the puller is slidably engaged on the base and used to affect tension in the spring by slidably moving the puller between the proximal and distal ends. In some embodiments, the puller is slidably mounted distal to the pusher. However, in certain embodiments, for example where the pusher and puller are slidably engaged on different track systems on the base, the puller need not be slidably mounted distal to the pusher. In various embodiments, the puller can be any form sufficient for the purposes in the pump assembly. By way of example and not limitation, the puller can comprise a puller block or puller sled, wherein the block or sled slidably engages the track system through the puller guide element. In certain embodiments of the puller block or puller sled, the first end portion of the spring is attached to the puller and the puller mates slidably with track guide of the track system. In certain embodiments, the puller mates slidably with the first track guide and the second track guide of the track system, for example channels on the inside side edges of the second base section. In some embodiments, the puller can have wheels, rollers, or bearings, particularly micro wheels, micro rollers, or micro bearings, attached to the puller, such as to the bottom of the puller, to reduce the friction on the puller as it slidably moves in the base. In other embodiments, the puller comprises a puller spring housing and a puller spool, wherein the puller spool is mounted in the puller spring housing, and the spring is coiled around the puller spool. In some embodiments, the puller spool is a drum, or in other embodiments, a shaft, where the spring, in particular a tape or ribbon spring is coiled around the drum or the shaft. In other embodiments, the spring is attached to the puller without being coiled around the puller spool.

The spring for use in the pump assembly can be any suitable spring. In particular, the spring as configured in the pump assembly generates a substantially constant force. In some embodiments, the spring comprises a tape spring or ribbon spring. In certain embodiments, the spring is an extendable negator spring. In some embodiments, the spring for use in the pump assembly is a single spring. In other embodiments, the spring in the pump assembly comprises two or more springs. Where multiple springs are used, in some embodiments, the springs are substantially similar and generate substantially similar constant force. In other embodiments where multiple springs are used, the two or more springs are different springs, such as of different dimensions, lengths, and/or different constant force. In various embodiments, the springs, in particular the substantially constant force springs can be made of metal, such as stainless steel, high carbon steel, nickel chromium alloy, nickel titanium alloy, or made of non-metal composites (see, e.g., U.S. Pat. No. 4,464,216, incorporated herein by reference). In some embodiments, the spring is made of shape memory alloy. In certain embodiments, the constant force spring is selected from a spring with about 5 to about 9 pounds of force such as about 6 to about 8 pounds of force. In certain embodiments, the pump may exert a pressure from about 5 psi to about 15 psi, such as about 11 psi to about 14 psi, or such as about 12 psi to about 14 psi. In certain embodiments, the pump may exert a pressure of about 5 to about 14 psi, such as about 13.5 psi.

As discussed above, the spring is attached to the puller at a first portion of the spring and attached to the pusher at a second portion of the spring such that moving the puller distally with respect to the pusher creates tension in the spring when there is resistance against movement of the pusher. In various embodiments, the spring is attached to the puller at a first end portion of the spring and attached to the pusher at a second end portion of the spring. In some embodiments, the spring can be attached to the puller at a distal position of the puller to create tension in the spring even when the cover is fully opened position. In other embodiments, the puller can be elongated and the spring attached at any point on the elongated puller, such as at the distal end, to provide variations in the tension with the pusher when the cover is fully opened. In certain embodiments, the spring is coiled around the pusher spool and attached to the puller at the first end portion. In other embodiments, the spring is coiled around the puller spool and attached to the pusher at the second end portion. The direction of coiling when the spring is coiled around the puller spool or the pusher spool is such that moving the puller distally can introduce tension in the spring and applies force on the pusher distally. In some embodiments, the spring is coiled around the puller spool and the pusher spool. In certain embodiments, a tape spring is attached to the puller at a first end portion, the pusher at a second end portion, and coiled around the spool on the pusher such that the tape spring produces substantially constant force on the plunger head when the coiled tape spring is unwound by moving the puller distally.

In some embodiments, the pump assembly further comprises a collar for centering and/or holding the chamber body seated in the base, wherein the collar is positioned on the base distal to the pusher. In various embodiments, collar is adapted for centering and/holding a syringe barrel. In certain embodiments, the collar has a surface which is adapted to receive the end piece of the chamber body, also referred to as the finger flange, in particular the end piece or finger flange of a syringe barrel. As such, in some embodiments, the collar has a recessed space which is complementary to the end piece. The collar can be adapted to receive a single end piece or finger flange, or adapted to receive two or more different sized end pieces or finger flanges. For example, the collar can have an outer recess dimensioned to receive a first end piece, and an inner recess dimensioned to receive a second end piece, where the second end piece is smaller than the first end piece. In certain embodiments, a stepped-recess can be used in a single collar to receive end pieces of varying sizes, wherein the recesses are stepped to smaller recesses from the distal to proximal direction, and wherein each recess receives an end piece differing in size from the other recesses. In various embodiments, the collar can be an open collar or a closed collar. In certain embodiments, where the collar is an open collar, the collar includes a slot adapted for receiving the finger flanges of a chamber body, e.g., finger flanges of a syringe barrel.

In typical embodiments, the collar is slidably engaged on the base. In some embodiments, the collar is slidably engaged on the first base section or the second base section, preferably the first base section. In some embodiments, the collar is slidably engaged on any of the track systems described herein. In certain embodiments, the collar is slidably engaged on a track system different from the track system to which the puller and pusher are slidably engaged. In other embodiments, the collar is slidably engaged on the same track system to which the puller and pusher are slidably engaged. As such, in certain embodiments, the collar further comprises a collar guide element, such as described for the puller and pusher guide elements, for slidably mounting the collar on the base. In other embodiments, the collar is dimensioned to fit the base and slidingly engage the base. The collar can be allowed to slide freely on the base, distally and proximally.

In some embodiments, a collar spring or elastic band can be used to press the collar against the end piece or finger flange of the chamber body. In certain embodiments, the collar spring or elastic band can be positioned distal to the collar or proximal to the collar. In typical embodiments, a collar spring is used. In some embodiments, the collar spring comprises a compression spring positioned proximal to the collar. In some embodiments, the collar spring contacts the collar at a first end of the collar spring and contacts the base at a position proximal to the collar, for example, the proximal wall of the second section of the base, at a second end of the collar spring. The collar spring can be mounted on a channel, for example a C shaped cross sectional channel, or in other embodiments, the collar spring can be wrapped around a collar spring guide rod, which extends longitudinally. In some embodiments, the channel or guide rod used for the collar spring can be part of the track system used for slidably mounting the collar to the base.

In various embodiments, the pump assembly further comprises a collar stop for preventing movement of the collar distally at a defined position. In certain embodiments, the collar stop is made positionally adjustable. In other embodiments, the collar stop is adapted to receive the chamber body, particularly a syringe, more particularly the syringe barrel. In some embodiments, the collar stop is attached to the distal end of the track systems described herein. In some embodiments, the collar stop is attached to the open end of the second base section. Whether the collar stop is positionally adjustable, attached to the distal end of a track system, or attached to the open end of the second base section, in certain embodiments, the collar stop can be slidably engaged on a collar stop guide rail. In certain embodiments, for slidably engaging the collar stop on a guide track or rail, the collar stop can have a collar stop guide element, such as those described for the puller, pusher, and collar. In some embodiments, the collar stop guide track or rail is disposed on the first base section. In certain embodiments, for a collar stop which is attached to the open end of the second base section, the collar stop engages a base stop, as described herein, to prevent separation of the first base section and the second base section in the expanded position.

In embodiments where the pump assembly comprises a base, and a cover pivotally connected to the base, in certain embodiments, the cover is pivotally connected to the base by a hinge. Typically, the cover is connected to the proximal end of the base by a hinge. In certain embodiments, the hinge pivotally connects the second cover section to the second base section. In some embodiments, a single hinge is used. In other embodiments, the cover is pivotally connected to the proximal end of the base, in particular the second base section, by two or more hinges.

In typical embodiments, to dampen the opening motion of the cover, particularly when there is tension remaining in the spring, which can be relayed to the cover through the one or more linkages when the cover is being opened, the pump assembly further comprises a damper which dampens the opening motion of the cover. The damper can be separate from the hinge, and the damper pivotally coupled to the cover and the base. In some embodiments, the damper is integrated into the mechanism of the hinge; that is, the hinge comprises a damper. Whether separate or as part of the hinge, the damper can employ various types of dampening mechanisms. In some embodiments, the damper is a viscous damper, a fluid damper, or a rotary friction damper. See, e.g., U.S. Pat. Nos. 7,275,284; 6,829,807; 6,085,384; and 4,829,628, incorporated herein by reference.

In further embodiments, the pump assembly includes a latch assembly or a lock assembly for keeping the cover in the closed position, particularly when a chamber body having a plunger is seated in the base and the cover lowered to move the puller distally and provide constant force on the plunger head through the puller, or keep the cover in the closed position during storage of the pump assembly. The latch assembly or lock assembly can be located on the side of the housing, including both sides of the housing near or at the distal end. In some embodiments, the latch assembly or lock assembly is on or near the distal end of the housing, i.e., distal end of the base and the cover, such as the distal end of the first base section and the first cover section. Various types of latch assemblies or lock assemblies can be used, including, among others, rotary latch, bayonet latch, draw latch (e.g., over center latches, pull draw latches, butt joint fastening latches), slide latch, magnetic latch, pin lock, bayonet lock, rotary latch lock, and the like. In some embodiments, the latch system can comprises a screw, nub, mound, or protrusion, which mates with a depression, indentation or hole to resist opening of the cover. For example, a nub or mound can be present on the inside face of a flange on the distal wall of the first cover section, wherein the flange overlaps the distal wall of the first base section when the cover is closed; and a depression complementary to the nub or mound is present on the outside face of the distal wall of the second cover section, wherein closing the cover engages the nub or mound on the flange on the first cover section onto the depression on the distal wall of the second cover section.

In some embodiments, the housing has a luer locator for receiving and/or locking the tip of the syringe onto the housing, in particular the base of the pump assembly. In certain embodiments, the luer locator is dimensioned to receive a luer type outlet of a syringe barrel. Typically, the luer locator is on the distal wall of the first base section. In certain embodiments, the luer locator comprises a collar on the distal wall of the first base section. The luer locator collar can be a partially cylindrical recess which receives a cylindrical luer lock tip of the chamber body and centers the outlet on the collar defining the luer locator. In various embodiments, the distal wall of the first cover section has an open collar, which with the luer locator on the distal wall of the first base section forms the opening on the housing for the outlet of the syringe. In various embodiments, the distal wall of the cover, in particular the distal wall of the first cover section, has an open collar, e.g., a partially circular collar, opposing the luer locator and/or open collar of the distal wall of the first base section to form the opening for the outlet when the housing is in the closed state.

In some embodiments, the distal wall of the base is also adapted to receive a disc luer connector, wherein the disc luer connector is attached to the outlet of a chamber body, e.g., a syringe. In various embodiments, the disc luer connector has a disc shaped flange to protect the luer connecting end from becoming contaminated during handling. In a preferred embodiment, the disc luer connector contains a filter for filtering out contaminating particulates and microbes in therapeutic fluids. An exemplary disc luer connector with filter is described in International application PCT/US15/16929, incorporated herein by reference. In certain embodiments, the disc luer connector contacts the inside face of the distal wall, which acts to brace the disc luer connector and connected syringe when force is applied to the syringe plunger. In other embodiments, the distal wall of the base has an open collar with a recessed space for receiving a disc portion of the disc luer connector. In certain embodiments, the distal wall has a partially circumferential flat surface on the inside face of the distal wall, around the luer locator collar, for contacting or receiving the disc luer connector.

In some embodiments, to prevent the use of non-fitting chamber bodies, e.g., non-fitting syringes, the pump assembly further comprises a rejector for rejecting a non-fitting chamber body. In various embodiments, the rejector comprises one or more rejector ramps at the distal wall adapted to receive the syringe outlet. In various embodiments, the rejector ramps are sloped upwards towards the distal wall and cause non-fitting syringes to slide out of the base when the cover is lowered and force applied to the plunger head. In certain embodiments, the rejection ramps can be formed of a sloped plate, or sloped ribs extending downward from the distal wall to the base from the distal to proximal direction, or alternatively, angled downward from the distal end to the proximal end. In some embodiments, the rejector ramps comprise spaced apart angled ribs or spaced apart sloping walls extending downward from the distal wall, and is sufficiently spaced apart to allow seating of syringe barrels with defined diameters. In various embodiments, the rejector can be configured to reject different chamber bodies, and a single pump assembly can have different rejectors for rejection of different chamber bodies.

In some embodiments, the pump assembly further comprises a means for hanging or holding the pump assembly. In various embodiments, the pump assembly has a strap, cord or chain for hanging or holding the pump assembly. In certain embodiments, the strap is a shoulder harness, or a strap that wraps around the body. In other embodiments, the strap is a loop strap. In some embodiments, the pump assembly has a clip for clipping the pump assembly onto a support structure. In an embodiment, the clip is a belt clip.

The pump assembly is preferably lightweight yet made of durable materials, e.g., aluminum, plastic, or combinations thereof. The components of the pump may comprise any suitable materials such as metal or plastics or any combination thereof. In certain embodiments, the cover and the base of the pump comprise a metal such as aluminum, e.g., 6000 series aluminum. The aluminum can have a hard coating and/or anodization. The lower end cap and upper end caps, when present, can be made of a plastic such as an impact resistant plastic, e.g., acrylonitrile butadiene styrene (ABS). In certain embodiments, the cover and the base are made from durable rigid plastic or impact resistant plastic, and certain other parts, such as the track guides, made from metal, such as aluminum. As will be understood by those skilled in the art, various lubricants can be used in the pump assembly to reduce friction on moving parts, such as the pusher, puller and collar.

When the pump assembly is not in use, it reduces to a compact size suitable for storage and/or portability. To use the pump, the housing is expanded by slidably moving the housing from the compacted position to the expanded position, the cover opened and a chamber body having a plunger, in particular a syringe barrel with a slidably disposed plunger, seated in the base. When the cover of the pump is closed, the puller is moved distally such that the syringe plunger receives a constant force from the pusher, and the contents of the chamber are expelled through the outlet of the chamber body. When the cover of the pump is fully opened, the puller is slidably moved proximally, thereby releasing the pusher from the head of the plunger such that the plunger does not receive force, and the chamber contents are not expelled. Thus, the pumping of any fluid from the pump assembly can be stopped by opening the cover and raising it to its fully opened position. When the administration is complete, the chamber body having the plunger may be removed and the pump may be transformed back into its compacted state for storage and/or portability.

Certain exemplary embodiments will now be described to provide an overall understanding of the principles of the structure, function, manufacture and use of the devices and methods disclosed herein. One or more examples of these embodiments are illustrated in the accompanying figures. Those of ordinary skill in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the pump assembly disclosed herein.

Accordingly, an embodiment of the pump assembly is illustrated in FIGS. 1 to 13. While the pump may have any size, shape or configuration, in the embodiment in FIGS. 1 to 13, pump assembly 100 is shown in the form of a substantially rectangular-shaped housing. In FIG. 1, the illustrated pump assembly is shown in the telescoped position with the cover open, while in FIG. 2, the pump assembly is shown in the telescoped position with the cover closed. The pump assembly 100 comprises a housing having a distal end 102 and a proximal end 101, wherein the housing includes a base 128 and a cover 500. The base comprises a first base section 103 and a second base section 104, where the first base section and the second base section are in sliding engagement such that the first base section and the second base section are slidingly movable relative to each other from a compacted position to an expanded (telescoped) position. The first base section 103 has a first pair of opposing base side walls 106 and 107 (the side having the side wall 106 is also referred to as a front edge and the side having the side wall 107 is referred to as a back edge), a distal wall, also referred to as a lower end cap 116, and an open end opposite the lower end cap. The second base section has a second pair of opposing base side walls 109 and 110; a proximal end occupied by a hinge assembly 600, as further described herein, or alternatively a proximal wall; and an open end opposite the proximal end.

Figure 3:
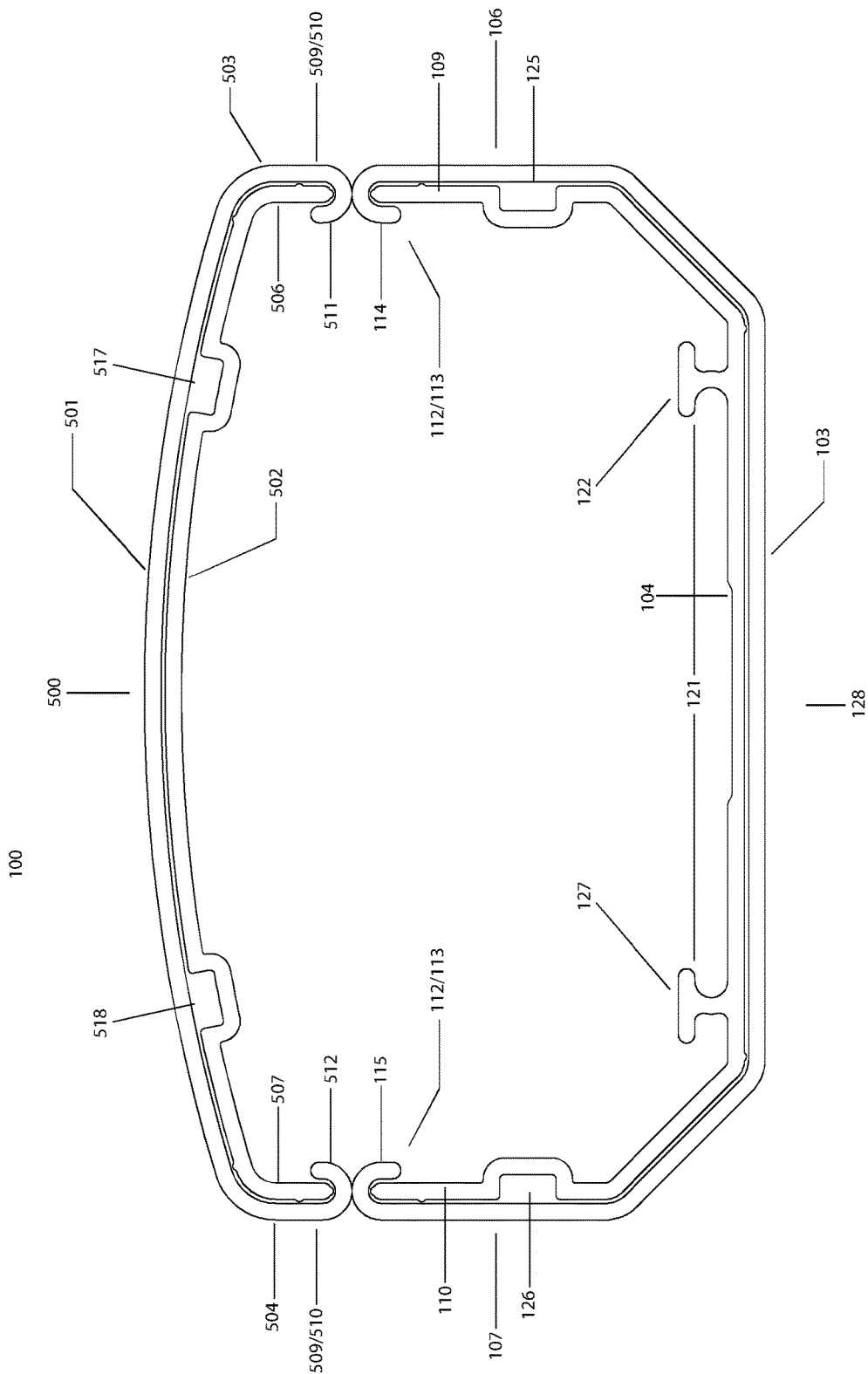
FIG. 3 is a cross-sectional end view of the pump assembly of FIG. 1 in a closed compacted state, depicting the arrangement of the first cover section and second cover section in sliding engagement, and the first base section and the second base section in sliding engagement.

The first base section 103 and the second base section 104 are in sliding engagement through a base guide system, which is illustrated in FIG. 3. In FIG. 3, the first base section 103 and the second base section 104 are in telescoping relation to each other. That is, the second base section mates slidably into the first base section such that the first base section and second base section are slidingly movable relative to each other. The first base section 103 is in sliding engagement with the second base section 104 along each side wall of the pair of side walls 106 and 107 of the first base section. In FIG. 3, the first base section has lips or edge flanges 114 and 115 on the sidewalls 106 and 107, respectively, of the pair of sidewalls of the first base section 103 to hold the corresponding sidewalls 109 and 110 of the second base section, and allow the first base section 103 to slidably move relative to the second base section 104. The lips or edge flanges 114 and 115 of the first base section 103 can extend inward in a C- or U-shape around one side wall (i.e., forward edge) 109 and the other side wall (i.e., back edge) 110 of the of the second base section 104.

Figure 4:
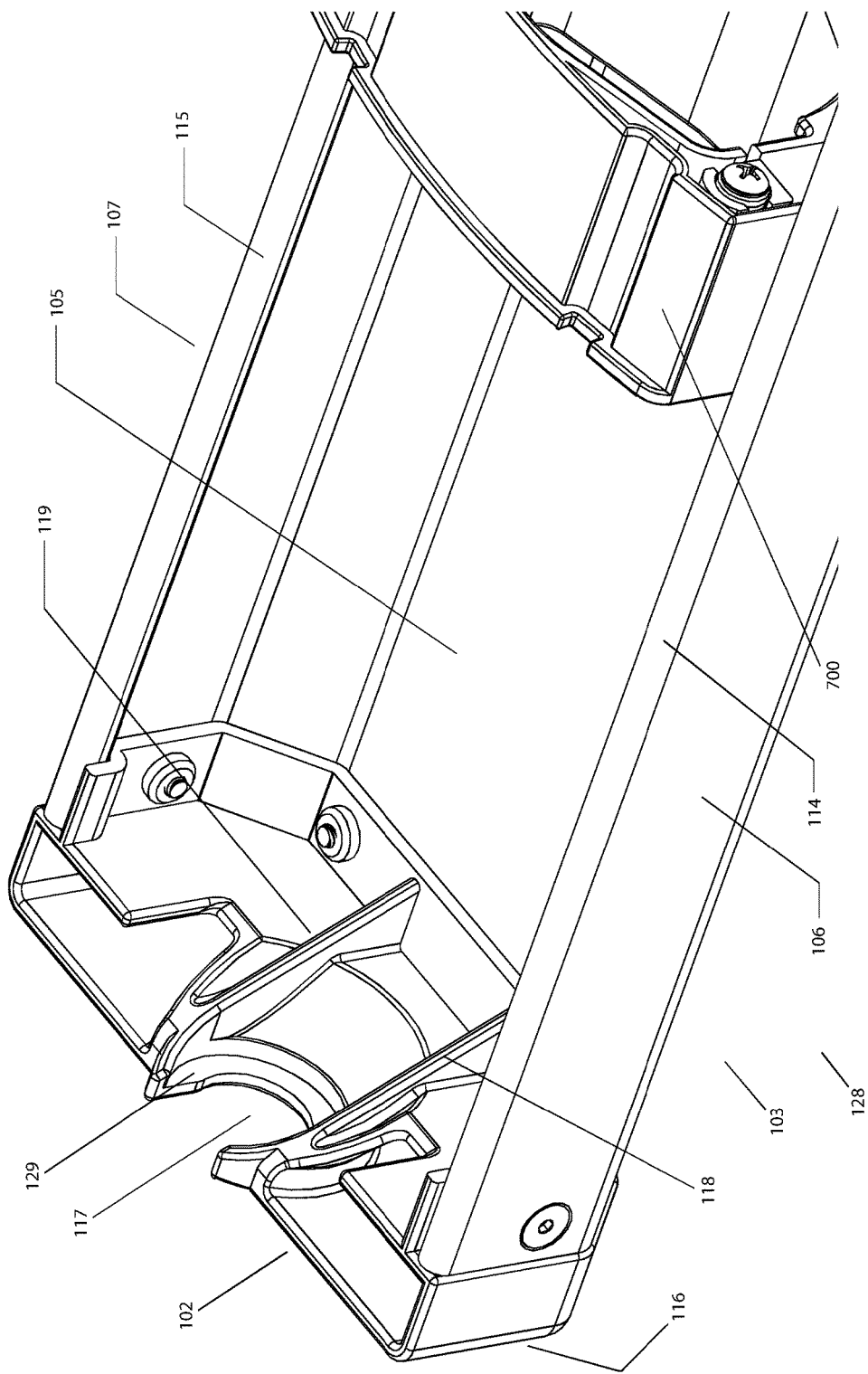
FIG. 4 is a perspective view of the pump assembly of FIG. 1 in its open telescoped state depicting the distal end of the interior of the base.

As shown in FIG. 4, the distal wall as defined by the end cap 116 of the base has a luer locator 117 for receiving or locking the tip of a syringe onto the housing, and in particular dimensioned to receive a luer type outlet of a syringe barrel. The luer locator 117 is an open collar dimensioned to receive a luer outlet of the syringe barrel. The distal wall also can have a partially circumferential surface 129 on the inside face of the distal wall, around the luer locator collar, for contacting or receiving the end of the chamber body defining the outlet, or a disc luer connector. In certain embodiments, the partially circumferential surface is a partially circumferential flat surface to accommodate a disc luer connector, and brace the disc luer connector when it is connected to a syringe and pressure is applied on the plunger head. The distal wall also has a pair of rejector ramps 118 and 119, which angle downward from the distal end to the proximal end, and is sufficiently spaced apart to allow seating of chamber body, e.g., syringes, with defined diameters but not chamber bodies, e.g., syringes, that do not fit within the spaced apart rejector ramps.

Figure 2:
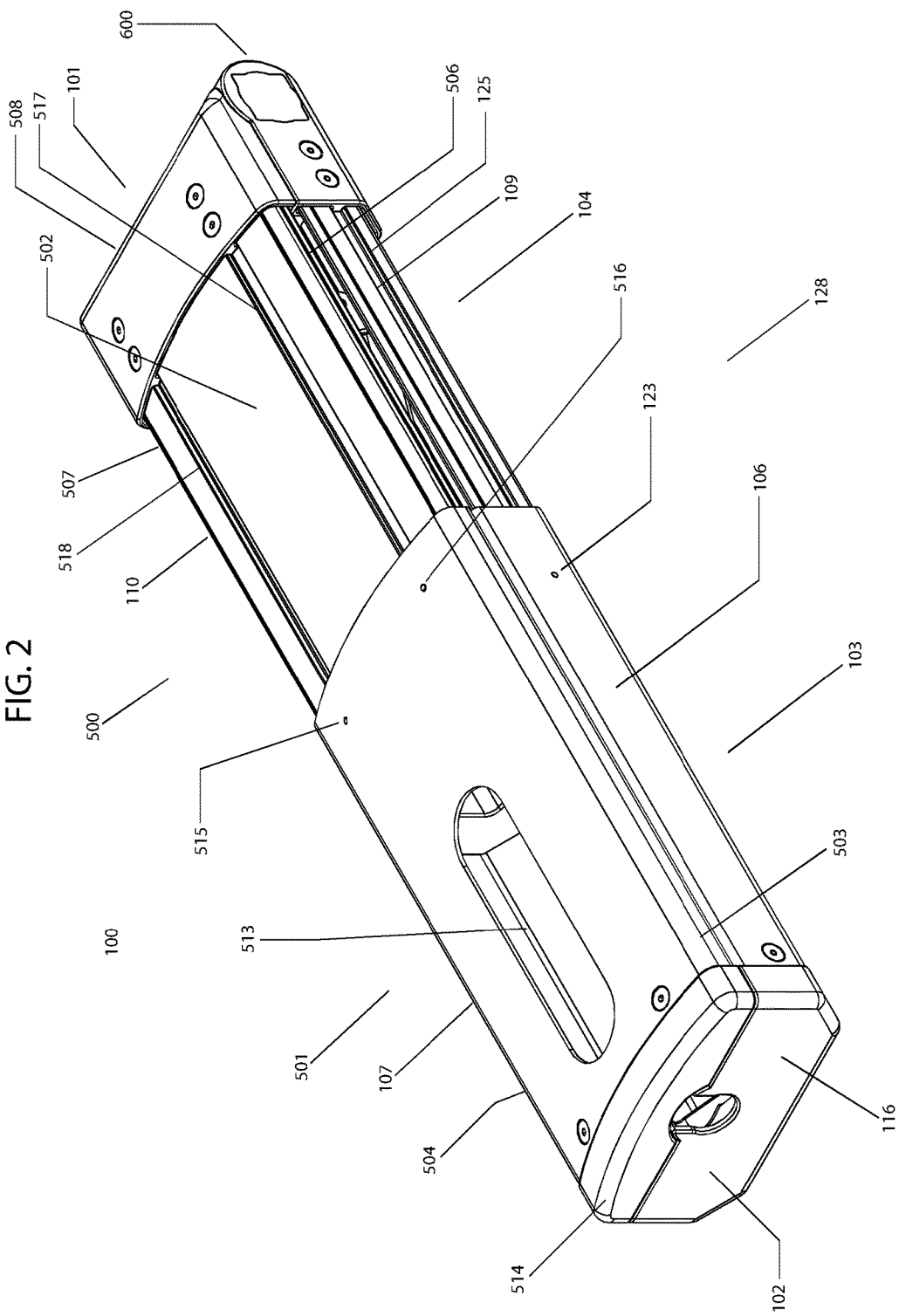
FIG. 2 is a perspective view of the pump assembly of FIG. 1 in a closed telescoped state.

In the pump assembly illustrated in FIGS. 1 and 2, the cover 500 includes a first cover section 501 and a second cover section 502, where the first cover section and the second cover section are in sliding engagement such that the first cover section 501 and the second cover section 502 are slidably movable relative to each other from a compacted position to an expanded position. In the embodiment of FIG. 1, the first cover section includes a first pair of opposing first cover section side walls 503 (i.e., front edge) and 504 (i.e., back edge), a first cover section distal wall, also referred to as a cover end cap 514, and an open end opposite the first cover section distal wall. The second cover section includes a second pair of opposing second cover section side walls 506 (i.e., front edge) and 507 (i.e., back edge), a second cover section proximal end 508, which can be occupied by a wall or the hinge 600, and an open end opposite the proximal wall. The cover includes a progress window 513, which permits viewing into the internal cavity of the pump, in particular to view the chamber body when in use. In the illustrated embodiment, the progress window 513 is present on the first cover section, towards the distal end of the housing.

The first cover section 501 and the second cover section 502 are in sliding engagement through a cover guide system, as illustrated in FIG. 3. In FIG. 3, the first cover section 501 and the second cover section 502 are in telescoping relation to each other. That is, the second cover section mates slidably into the first cover section such that the first cover section and second cover section are slidingly movable relative to each other. In certain embodiments, the first cover section 501 is in sliding engagement with the second cover section 502 along each side wall of the pair of opposing side walls 503 and 504 of the first cover section. In FIG. 3, the first cover section has lips or edge flanges 511 and 512 around the sidewalls 503 and 504 of the pair of opposing sidewalls of the first cover section 501 to the corresponding sidewalls 506 and 507 of the second cover section 502 and allow the first cover section 501 to slidably move relative to the second cover section 502. The lips or edge flanges 511 and 512 of the first cover section 501 can extend inward in a C- or U-shape around one side wall (i.e., forward edge) 506 and the other side wall (i.e., back edge) 507 of the of the second cover section 502. In a closed compacted state, the first cover section 501 is in its most proximal 101 position and the first cover section 501 overlays the second cover section 502 (see FIG. 6). In a closed compacted state, the progress window 513 of the first cover section can be blocked by the second cover section. In a closed telescoped state, the first cover section 501 is extended in a distal direction away from the proximal hinge 600, and the second cover section 502 is substantially exposed and non-overlapping with the first cover section 501 (see FIG. 2). In certain embodiments, the cover 500 is not expandable to a telescoped state. For example, the cover 500 cannot expand to a telescoped state and there is no second cover section on the pump assembly 100 on which the cover may extend.

Figure 6:
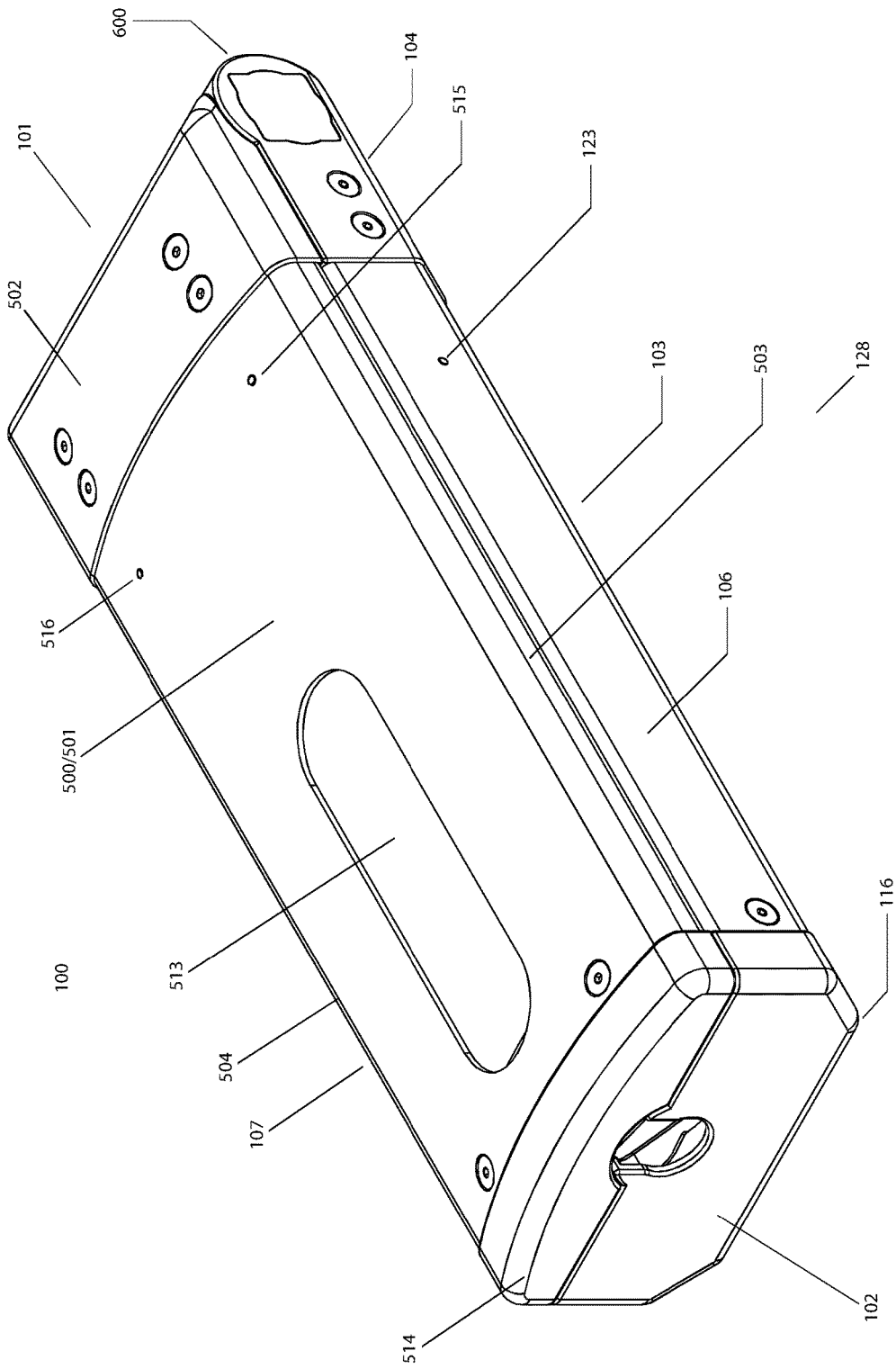
FIG. 6 is a perspective view of a closed compacted state of the pump assembly of FIG. 1.
Figure 7:
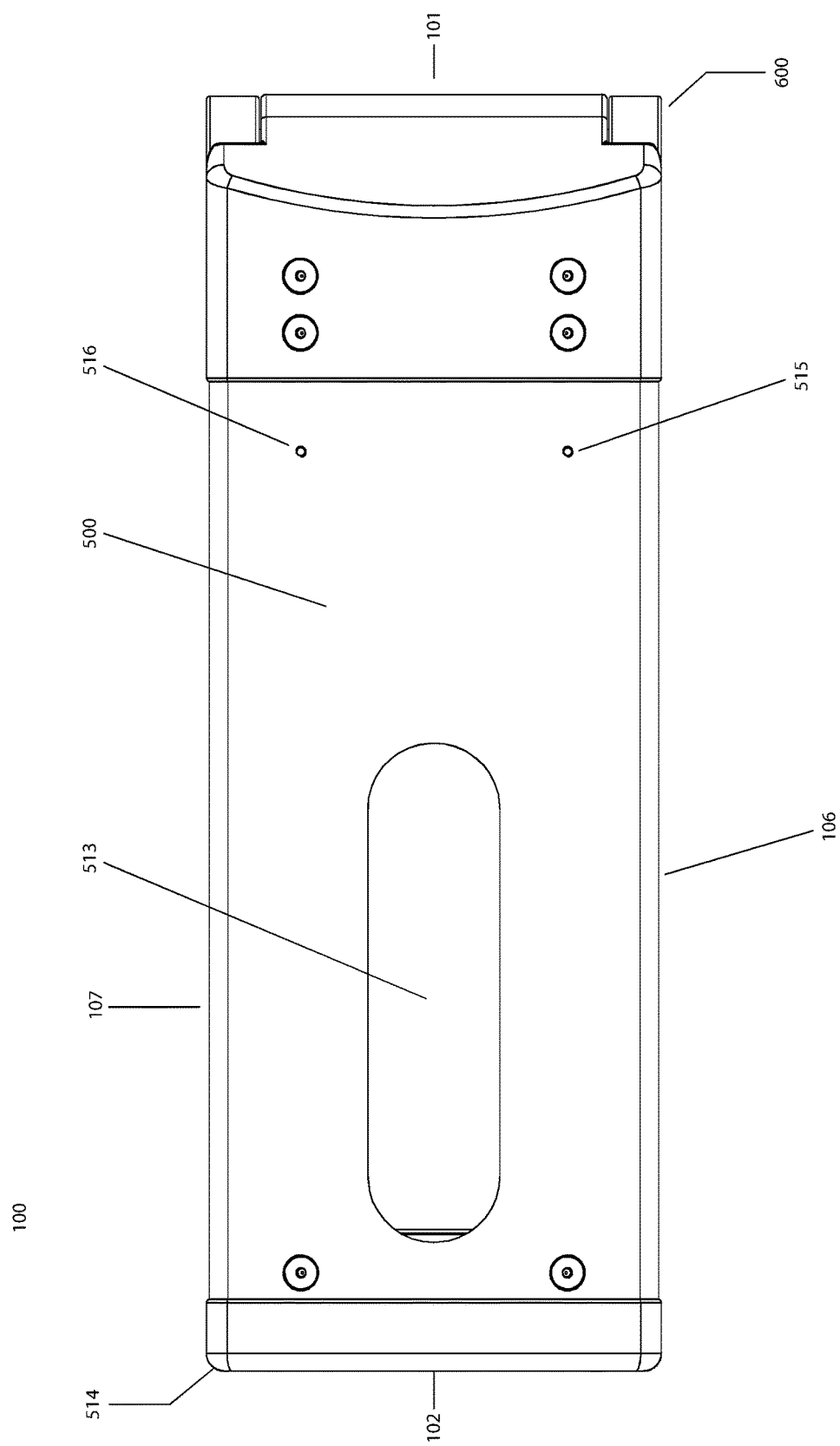
FIG. 7 is a top elevational view of a closed compacted state of the pump assembly of FIG. 1.
Figure 8:
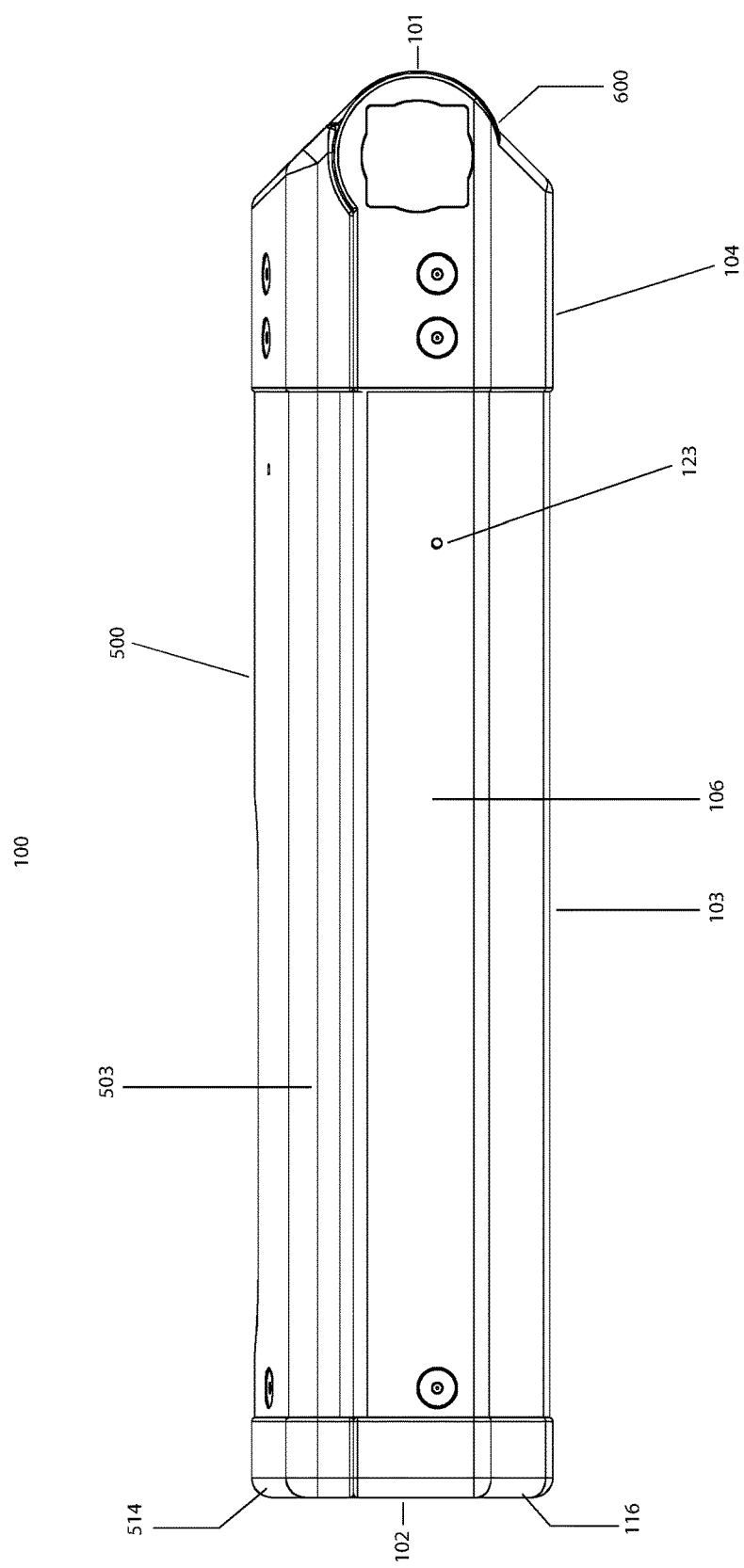
FIG. 8 is a side elevational view of a closed compacted state of the pump assembly of FIG. 1.

In the embodiment of FIGS. 1 to 13, the cover 500 is pivotally connected to the base 128 by a proximal end hinge 600, which has a damper 601 to effectuate slow and/or controlled opening of the cover 500. In the illustrated embodiment, the second base section 104 is pivotally connected by the hinge to the second cover section 502 at the proximal end 101 of the second base section and the second cover section. The hinge 600 allows the cover to be raised or lowered and the damper 601 dampens the opening of the cover, particularly if there is tension remaining in the spring when the cover is being opened. For example, a user may depress a button releasing a latch holding the base end cap 116 and cover end cap 514 in contact or manually separate the cover and base. Once released, the cover 500 can hinge open in a slow and/or controlled matter, for example, without the need for manipulation by the user. In certain embodiments, a spring clutch on the shaft of the damper allows for the dampening force to act in one direction only, therefore limiting the amount of force needed to close the cover 500. The hinge 600 connects the cover 500 to the base 128 such that slidably moving the second base section 104 relative to the first base section 103 moves together the second cover section 502 relative to the first cover section 501 when the cover is in the closed position. However, each of the cover 500 and the base 128 can telescope or retract independently of the other when the pump is in the open state. For example, in an open state, the base 128 may be telescoped to receive a syringe while the cover 500 is in a retracted state in order to occupy less space and stay out of the path of a user preparing and inserting a syringe. The cover 500 can then be telescoped independently from the base 128. FIG. 2 illustrates the pump assembly in the closed telescoped position, while FIGS. 6, 7 and 8 illustrate the pump assembly in the closed compacted position.

Figure 5:
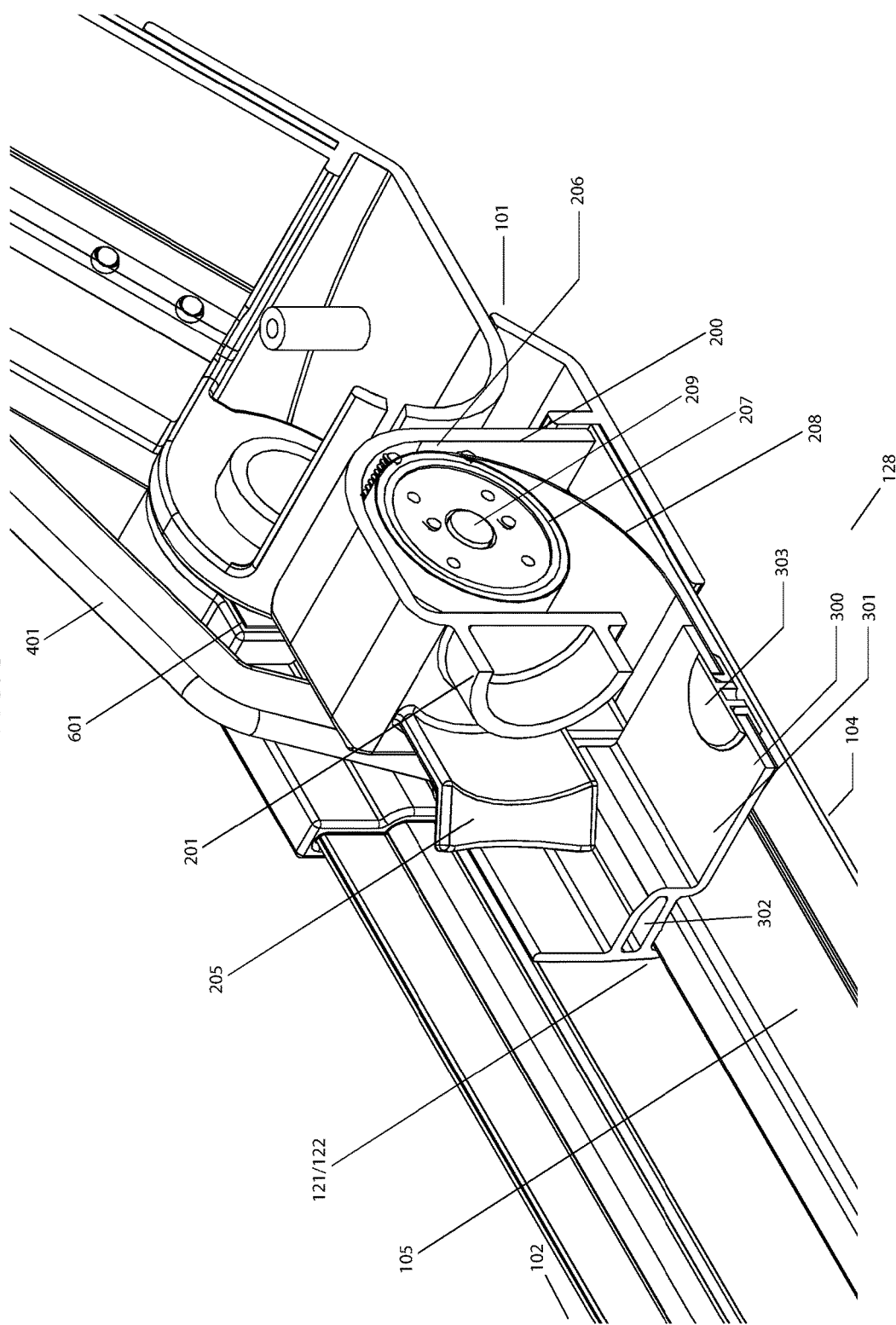
FIG. 5 is a perspective cross sectional view of the pump assembly of FIG. 1 depicting the interior of the pusher assembly with the spring spool and the connection of the spring to the puller assembly.

The pump assembly further includes: a puller assembly 300, which as shown in FIG. 5, is configured as a puller sled or plate 301 and is slidably engaged to the base 128; and a pusher assembly 200, which is slidably engaged to the base 128. In the embodiment shown, the puller 200 and the pusher 300 are slidably engaged to the second base section 104. A spring is connected 303 to the puller 300 at a first end portion of the spring and connected to the puller 200 at a second end portion of the spring. As provided in detail in FIG. 5, the pusher assembly includes a spring housing 206 and a spool 207, where the tape spring 208 is coiled around the spool. The tape spring can be directly attached to the spool, or the coil of tape spring allowed to sit on the spool without being directly attached to the spool. The spool 207 can be a spool drum mounted on a drum shaft 209. The pusher is dimensioned to contact the head of the plunger, which in FIG. 5, is a cylinder having a recessed internal space 201. For guiding the plunger head to the pusher, the pusher has a plunger centering structure in the form of centering wings 204 and 205, which angle inward towards the plunger head contacting portion 201, thereby guiding the plunger head to the plunger head contacting portion of the pusher assembly.

The puller 300 and the pusher 200 are in sliding engagement with the base 128. In FIGS. 1, 3 and 5, the pump assembly has a track system 121, which is comprised of a first track guide rail 122 and a second track guide rail 127 on the floor of the second base section 104. The track guide rails have a cross sectional T-shape, and extend longitudinally (proximal-distal) on the second base section. The puller 300 has puller guide elements 302, which are slidably engaged on the T-shaped track guide rails 122 and 127. The pusher 200 has pusher guide elements (not shown) which are also slidably engaged on the T-shaped track guide rails 122 and 127. Since the same track system is used by the puller 300 and the pusher 200, the puller 300 is slidably mounted on the track system and on the base distal to the pusher 200. That is, the puller assembly 300 is fixed relative to the pusher assembly 200 in a position closer to the distal end 102 of the base.

As depicted in FIG. 1, a first linkage 400 and a second linkage 401 pivotally couple the cover 500 to the puller 300, where the first pivot point 402 and second pivot point 403 of the first linkage 400 and the third pivot point 404 and fourth pivot point 405 of the second linkage 401 are positioned to slidingly move the puller towards the distal end when the cover 500 is lowered and slidingly move the puller towards the proximal end when the cover 500 is raised. In particular, the first pivot point 402 of the first linkage and the third pivot point 404 of the second linkage are on the second cover section. The first linkage 400 and the second linkage 401 are bent at an angle, in particular at a defined angle, towards the puller 300. The point of the bend 406 and 407 on the linkage is offset from the center of the linkage to provide a bent linkage with two sections, where the first section is shorter than the second section of the linkage. The bend can be located at a point on the linkage proximal to the puller assembly 300. As such, in the embodiment shown, the first section, which is the shorter section, is pivotally connected to the puller 300 while the second section, the longer section, is pivotally connected to the second cover section 502. In certain embodiments, to keep the movement of the first linkage 400 and second linkage 401 coordinated for the movement of the puller 300, the first linkage 400 and the second linkage 401 are substantially the same length, have a bend position at substantially the same point on the linkage, and have substantially the same defined bend angle. In addition, for substantially parallel movement of the first linkage and the second linkage in moving the puller, the positions on the cover for the pivotal attachment of the first linkage and the second linkage are at substantially the same distance from the proximal end, and the distance from one side edge (i.e., front edge) of the cover nearest the first linkage and the distance from the side edge (i.e., back edge) of the cover nearest to the second linkage are also substantially the same.

In the embodiment of FIG. 1, the base 128 in the expanded position has a base interior 105 dimensioned to fit a chamber defining an outlet and a bore, and a plunger slidably disposed in the bore. The pump assembly 100 optionally includes a collar 700 for centering and/or holding the chamber body. The collar 700 in FIG. 1 is a closed collar and slidably engaged to a collar guide system 704 on the base 128 by collar guide elements 707. The collar 700 can have a recess 705 for receiving the end piece (e.g., finger flange) of the chamber body, e.g., a syringe finger flange. A collar spring (not shown) or an elastic band, as further described herein, can be used to keep the collar pressed against the head of plunger.

In an exemplary embodiment of operating the pump assembly of FIGS. 1 to 13, to transform the pump from its closed compacted. state (see FIGS. 6, 7 and 8) to the closed telescoped state, the proximal end 101 can be clasped in one hand and the distal end 102 clasped in the other hand and the two ends pulled in opposite directions to extend the pump to its closed telescoped state (see FIG. 2). In telescoping the pump from its closed compacted state, the first base section 103 and the second base section 104 slidably move along the side walls 109 and 110 of the second base section and the edge flange guides 114 and 115 of the first base section 104 while the first cover section 501 and the second cover section 502 slidably move along the side walls 506 and 507 of the second cover section and the edge flange guides 511 and 512 of the first cover section. The cover and the base can be held by a locking or latching means at the distal end 102 so that the cover 500 and the base 128 extend together away from the proximal hinge 600 when the pump is extended. By way of example and not limitation, a locking or latching system includes, among others, a protrusion, a bump, a magnet or a latch on one of the base or cover end caps dimensioned to fit or designed to complement the other end cap and allow the cover and base to extend or contract together and not individually when the pump assembly is closed. In certain embodiments, the locking means does not hold the cover in a closed state but rather prevents proximal or distal movement of one of the cover or base relative to the other. For example, a locking assembly, such as a protrusion from the lower end cap received by an opening in the upper end cap, prevents the cover from extending without extending the base but the protrusion does not impede the opening of the cover.

The transformation of the pump from the closed compacted state to the closed telescoped state can be effectuated in ways other than manually pulling the two ends of the pump. For example, the first base section 103 and the second base section 104 can be spring loaded such that a trigger, such as the depression or sliding of a button, causes the compacted pump to expand to the closed telescoped state. As discussed above, the cover 500 and/or base 128 can have a locking means to lock the cover and/or base in its telescoped state. For example, the pair of opposing side walls 506 and 507 of the second cover section 502 can include a detent tab, wherein in the compacted state, the detent tab is compressed by the first cover section 501, and in the telescoped state the detent tab extends from the track, locking the first cover section in the extended position and preventing the cover from retracting (not shown). To retract the cover to its compacted state, the user may, for example, depress the detent tab or supply sufficient force on the distal end of the cover toward the proximal end of the cover to force the detent tab to compress between the track and the cover and transform the cover to its compacted state. In certain embodiments, detent elements 515 and 516 (see, e.g., FIG. 2) are also present on the first cover section and engage detent grooves 517 and 518 to stop the movement of the first cover section relative to the second cover section, particularly in the expanded state. The base also has detent elements on the side walls of the pair of opposing side walls of the first base section, and engage detent grooves present on the side walls of the pair of side walls of the second base section to stop the movement of the first base section relative to the second base section, particularly in the expanded state. FIGS. 1 and 2 show a detent element 123 on one side wall of the first base section (front edge) and the corresponding detent groove 125 on the sidewall of the second base section. FIG. 3 shows the detent grooves 125 and 126 in a cross sectional view.

To transform the pump from the closed to open telescoped state, the base end cap 116 can be clasped in one hand and the cover end cap 514 in the other hand and the two caps pulled away from each other. In certain embodiments, a locking or latching means holds the base end cap 116 and cover end cap 514 closed. The release or opening of the closing means may be triggered, for example, by depressing a button which releases a latch thereby allowing the caps 116 and 514 to separate. For example, a latch, clasp, or magnet can hold closed the base end cap and the cover end cap. Once the connection between the base end cap 116 and the cover end cap 514 is released, the cover can hinge open by way of the proximal end hinge 600.

Figure 9:
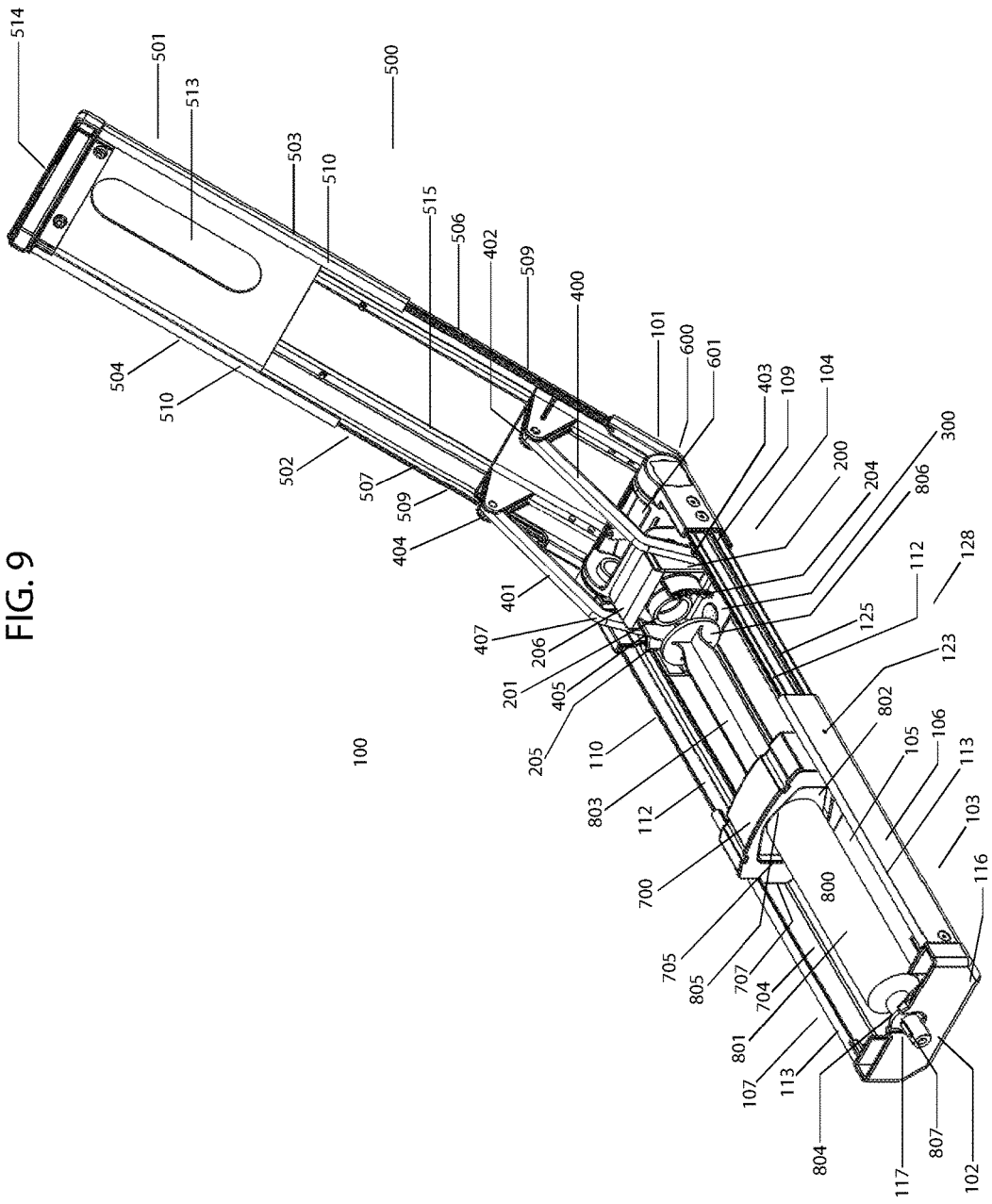
FIG. 9 is a perspective view of the pump assembly of FIG. 1 in its open telescoped state with a syringe seated in the base of the pump assembly.

As illustrated in FIG. 9, in the open telescoped state, a chamber body having a plunger, such as a syringe 800, is loaded into the interior of the base of the pump assembly 105. The base 128 can be adapted to receive a conventional syringe 800 comprising a syringe barrel 801 and a plunger 803. A conventional syringe 800 comprises a barrel 801 defining a lumen for receiving a plunger 803 with an outlet tip 804 at one end of the barrel 801 and a broad opening 805 at the other opening of the barrel 801. At the broad opening 805 of the barrel 801, a surface, also referred to as an end piece or finger flange 802 extends on the outside of the barrel 801 substantially perpendicularly to the surface of the barrel 801. The collar 700 is dimensioned to receive the end piece holding the syringe barrel 801 in place and preventing movement, e.g., lateral movement, of the syringe in the base interior 105. As illustrated in FIG. 1, the collar 700 can be in sliding engagement with a track system 704 on the base 128 through collar guide elements 707 and can have a tension means to keep the collar pressed against the end piece of the syringe barrel. For example, a spring or elastic band positioned on the base can be used to keep the collar pressed against the end piece of the syringe. The collar 700 can slide in the direction of the proximal end 101 or distal end 102. In certain embodiments, the collar 700 can be connected to the base 128 with a collar spring, which spring can be placed on the base either proximal or distal to the collar. In its resting state, the collar spring of the collar 700 can place the collar in a position closest to the distal end 102 of the base 128. In an expanded position, the collar 700 can be further from the distal end 102 of the base 128 and closer to the proximal end 101 of the base 128.

Figure 10:
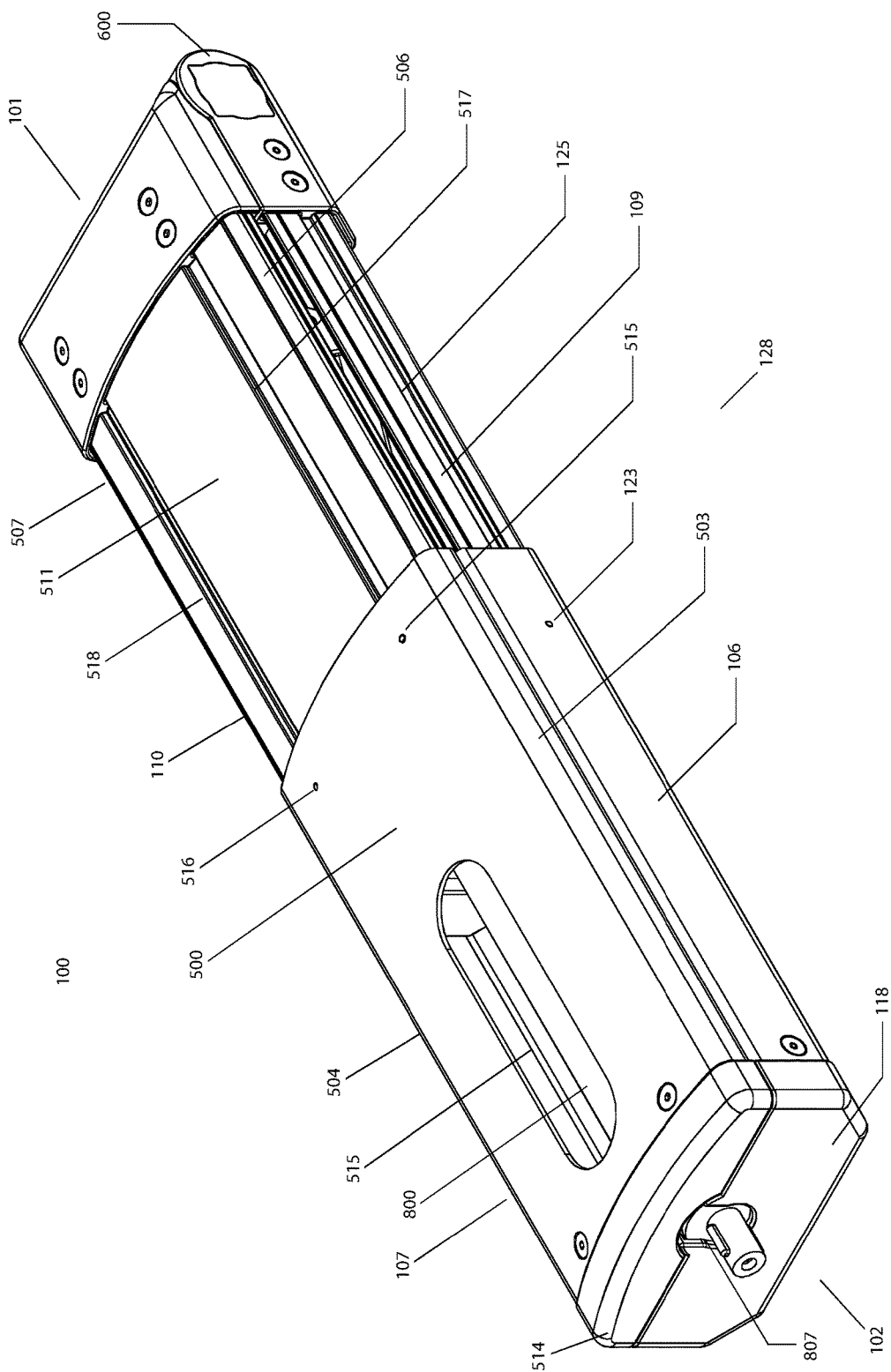
FIG. 10 is a perspective view of the pump assembly of FIG. 1 in its closed telescoped state with a syringe positioned in the base of the pump assembly.
Figure 11:
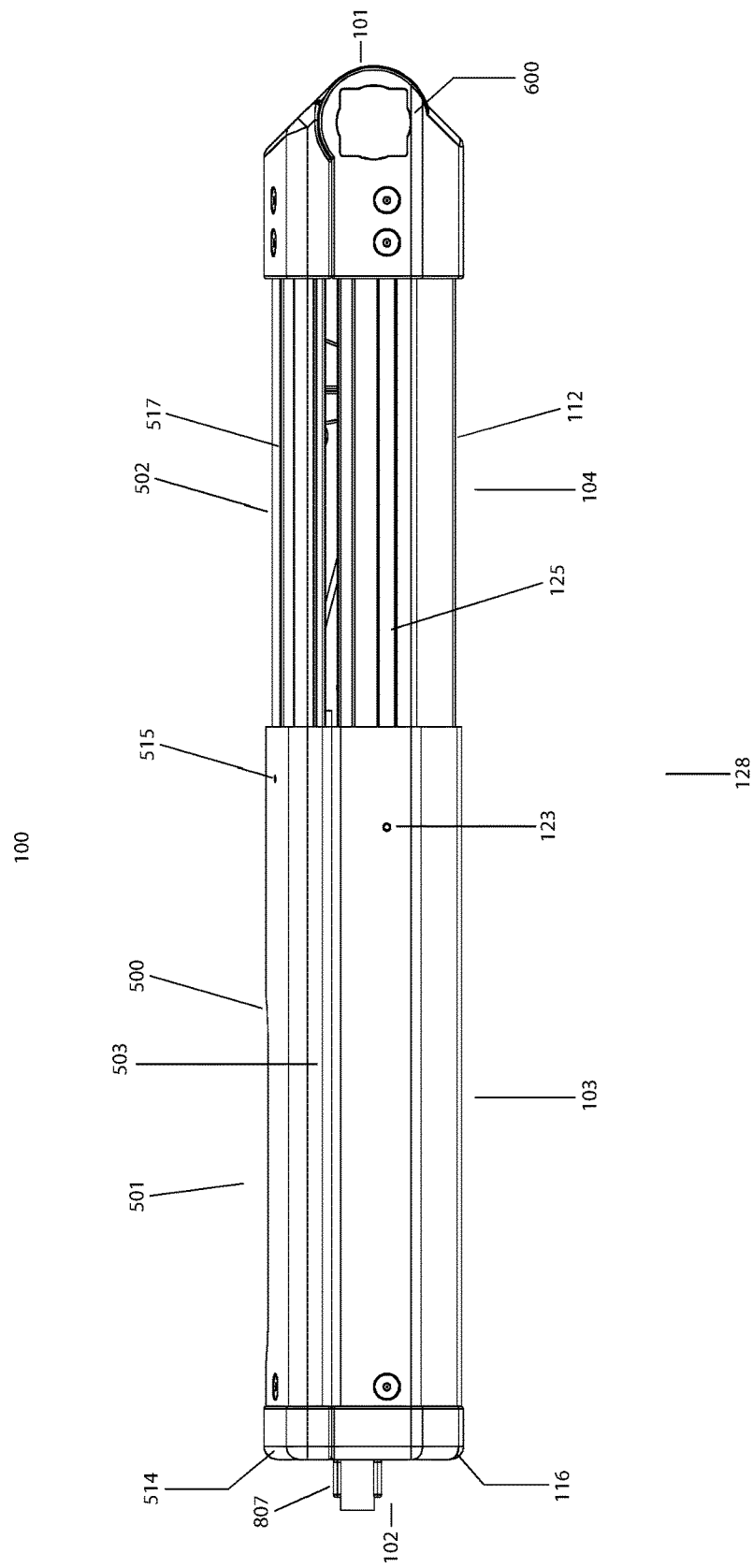
FIG. 11 is a side elevational view of the pump assembly of FIG. 1 in its closed telescoped state with a syringe positioned in the base of the pump assembly.
Figure 12:
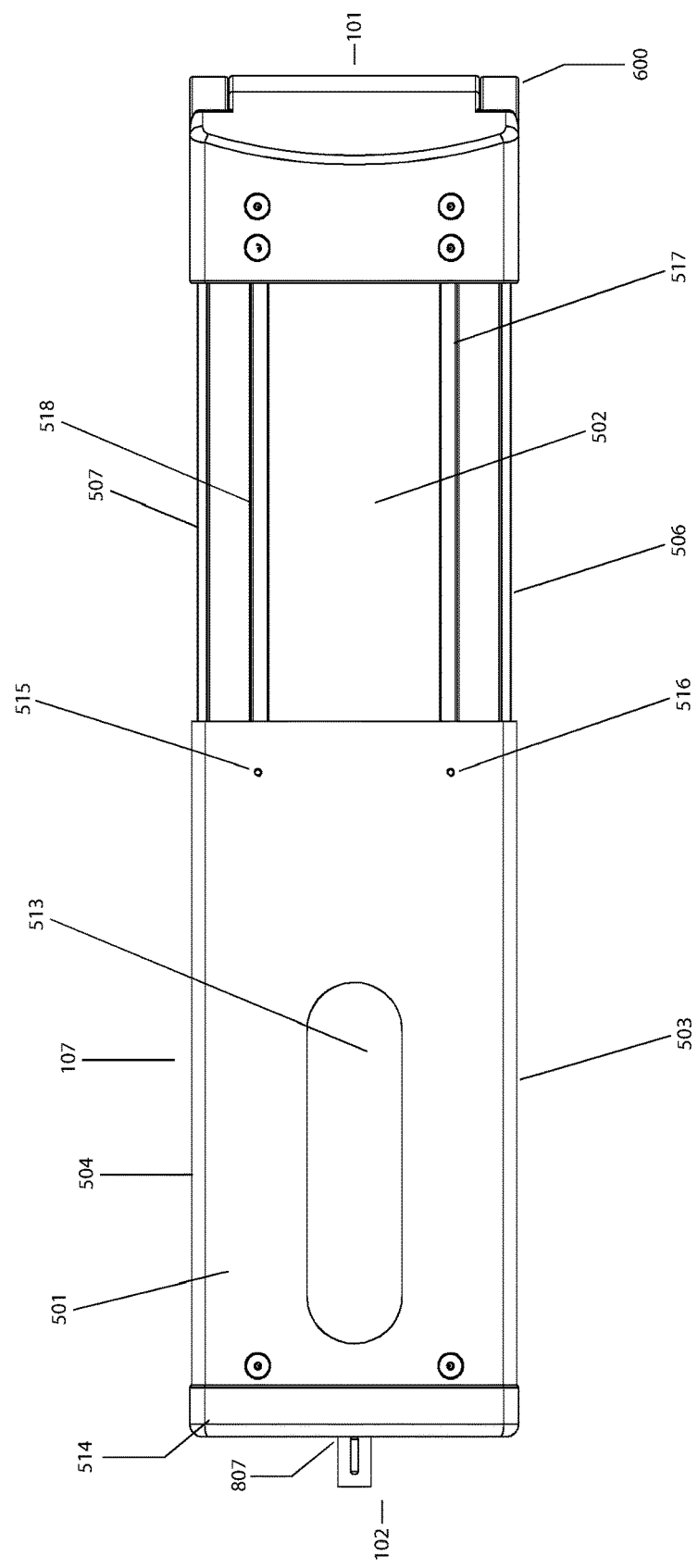
FIG. 12 is a top elevational view of the pump assembly of FIG. 1 in its closed telescoped state with a syringe positioned in the base of the pump.
Figure 13:
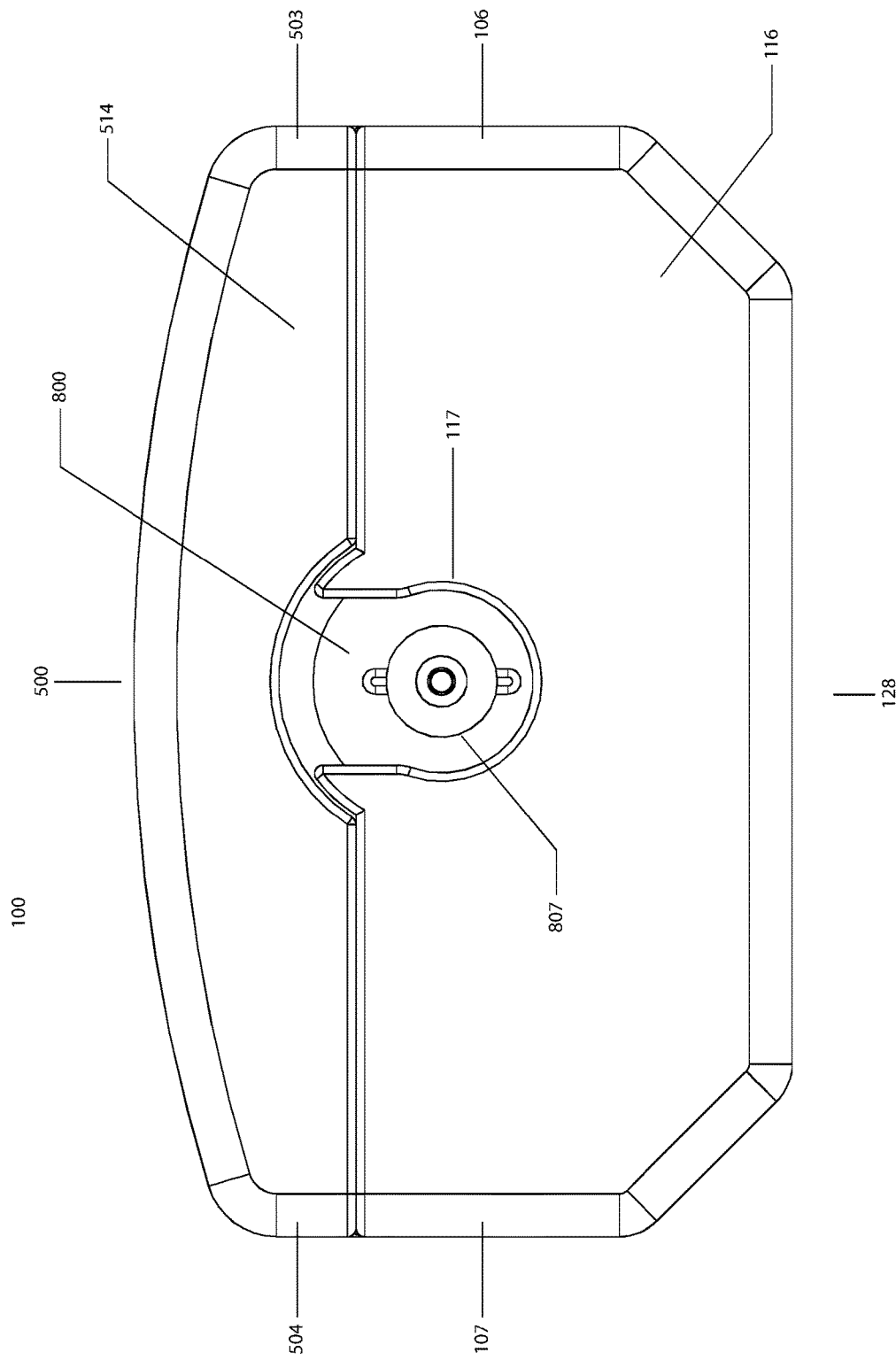
FIG. 13 is a view of the distal end of the pump assembly of FIG. 1 in its closed telescoped state with a syringe positioned in the base of the pump assembly.

In certain embodiments, such as in FIGS. 9 to 10, a female luer 807 is attached to the outlet tip 804 of the syringe 800. The female luer 807 is dimensioned to fit into the luer locator 117 of the base and prevent movement of the syringe 800. In certain embodiments, if a syringe 800 is loaded into the interior 105 and the syringe lacks the proper female luer 807 to fit within the luer locator 117, the syringe 800 will be pushed up out of the pump along rejection ramps 118 and 119 (see FIG. 4) when the user attempts to close the pump cover 500. By way of example and not limitation, if the user attempts to use a 30 mL syringe in a pump suited for a 20 mL syringe, the rejection ramps will eject the syringe from the base upon attempted closure of the cover.

In certain embodiments, a syringe 800 preloaded with a liquid is loaded into the base interior 105 of the pump. The preloaded syringe may be inserted plunger first through the syringe locating collar 700. The surface or end piece 802 can be held by the face of the collar 700 facing the distal end 102 of the base 128, and the head of the plunger 806 of the syringe 800 extends from the side of the collar 700 facing the proximal end 101 of the base 128. A female luer 807 can rest in or lock into the luer locator 117. The collar 700 can be slidably engaged on the track system 704 in the base 128 away from its rested state in a more proximal position, closer to the distal end of the base to accommodate the length of the syringe 800. A collar spring of the collar 700 causes the collar to be pressed onto the end piece 802 in the direction of the distal end 102 of the base to help secure the syringe in place.

In certain embodiments, the preloaded syringe is fitted with tubing suitable for administering the liquid in the syringe 800. Tubing for the syringe pump may be selected with different pre-set flow rates in order to achieve a final desired rate of infusion to the patient. The tubing can be attached to the female luer 807, preferably prior to the loading of the syringe 800 into the base of the pump. The tubing extends from the female luer to the outside of the pump. The end of the tubing that is not attached to the female luer can be attached to a needle or one or more additional tubes through connectors.

Once the syringe 800 is secured in the base of the pump, e.g., via the luer locator 117 and the collar 700, the cover 500 of the pump can be closed, as shown in FIG. 10, to begin the flow of the liquid. When the cover is in an open position, the pivotally coupling linkages 400 and 401 position the puller proximally in the base, and the pusher is not forced against the head of the plunger such that no liquid is forced out from the syringe. When the cover is lowered to a closed position, the pivotally coupling linkages 400 and 401 move the puller distally to force the pusher against the head of the plunger through the connected spring, and the plunger is pushed into the barrel of the syringe, thereby forcing liquid out of the syringe barrel. In certain embodiments, when the cover 500 remains closed and the syringe is not empty, the liquid will be forced out of the syringe barrel through substantially constant force imposed on the plunger 803 by the spring. If the pump cover 500 is opened, the pivotally coupling linkages 400 and 401 move the puller 300 and the pusher 200 proximally, thereby releasing the pusher 300 from the head of the plunger 803 and halting the flow of fluid out of the syringe barrel.

Figure 14:
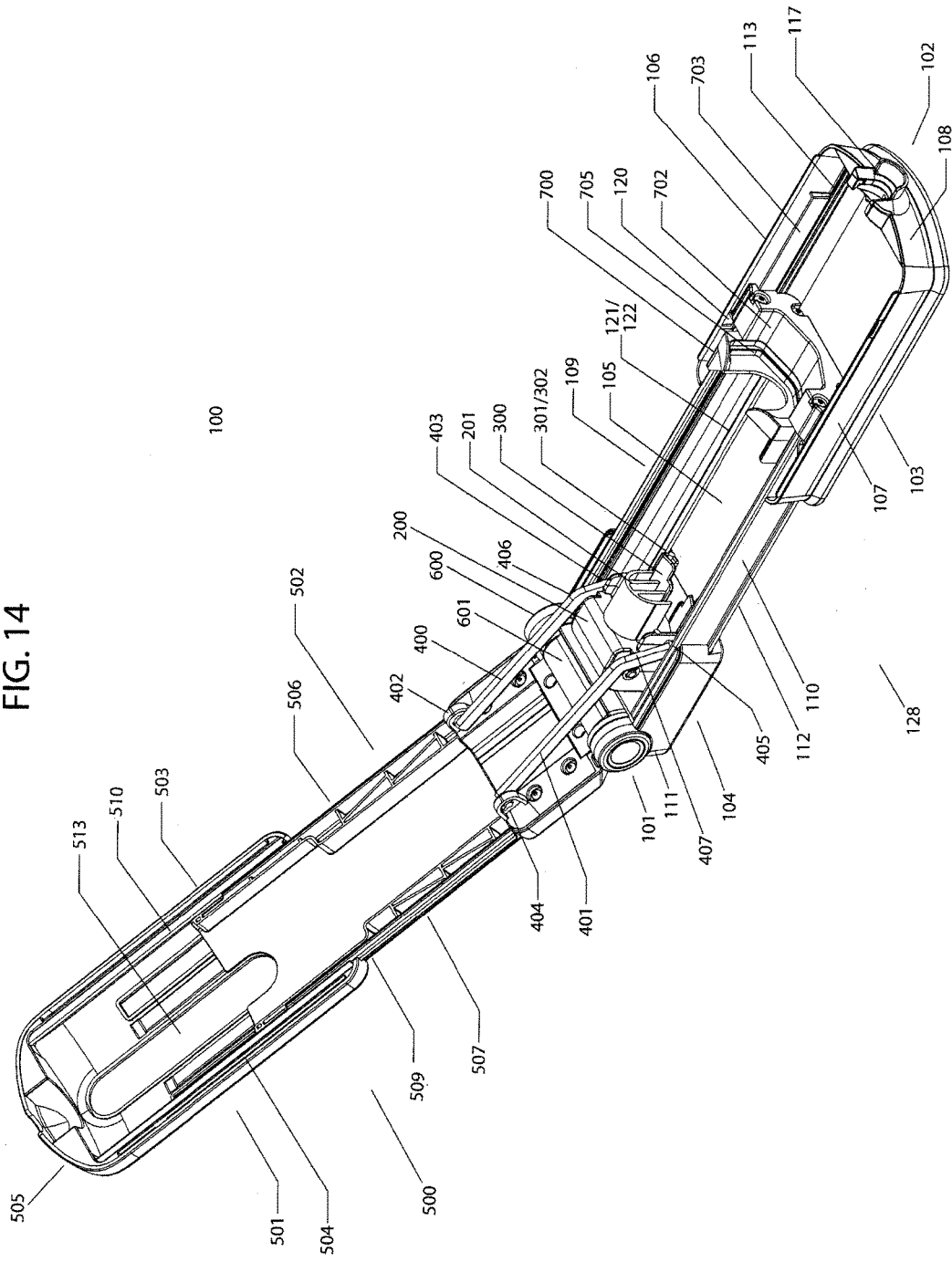
FIG. 14 is a perspective view of an alternate embodiment of the pump assembly of the disclosure in an open expanded state.

Another embodiment of the pump assembly is depicted in FIGS. 14 to 24, illustrating the different features and configurations that can be incorporated in the pump assembly. In FIG. 14, which shows the pump assembly in the open expanded position, the pump assembly 100 comprises a housing having a distal end 102 and a proximal end 101, where the housing has a base 128 and a cover 500. The base 128 includes a first base section 103 and a second base section 104, where the first base section is slidingly engaged to the second base section such that the first base section and the second base section are slidingly movable relative to each other between a compacted position and an expanded position. The first base section 103 has a first pair of opposing base side walls 106 (front edge) and 107 (back edge), a distal wall 108, and an open end opposite the distal wall. The second base section 104 has a second pair of opposing base side walls 109 (front edge) and 110 (back edge), a proximal wall 111, which can be part of the hinge 600, and an open end opposite the proximal wall. The base defines an interior space 105, which is sufficient to receive a chamber body having a plunger when the base is in the expanded position.

Figure 18:
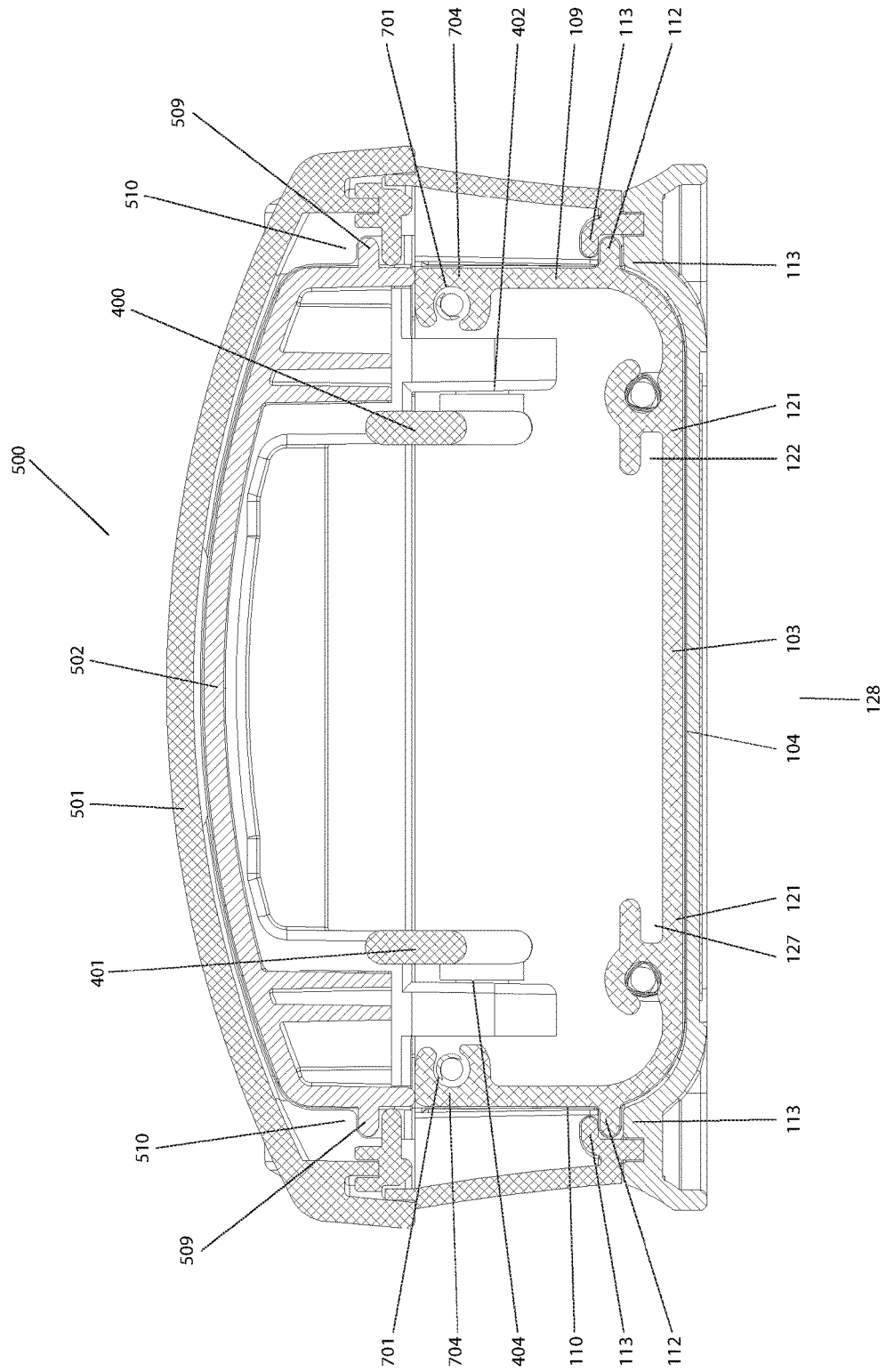
FIG. 18 is a cross sectional view from the distal end of the pump assembly of FIG. 14 in its closed compacted state.
Figure 19:
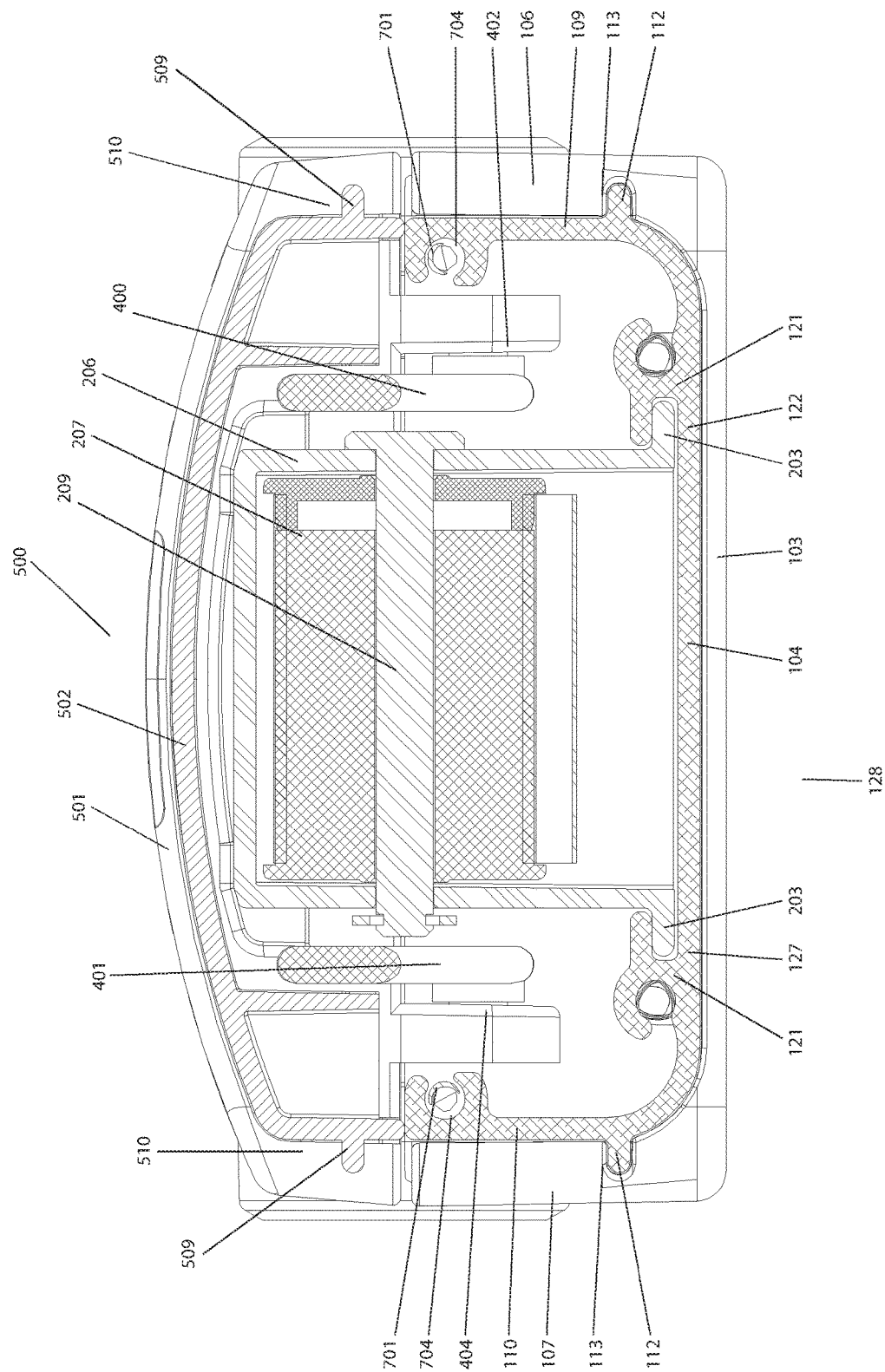
FIG. 19 is a cross sectional view from the distal end of the pump assembly of FIG. 14 in its closed compacted state, where the cross sectional view also shows the pusher assembly.

As illustrated in FIGS. 14, 18 and 19, the first base section 103 and the second base section 104 are in sliding engagement through a base guide system 121, which includes a base guide rail 112 on the second base section slidably engaged to the base guide track 113, which is a channel, on the first base section. The base guide rail 112 facing outward from the side wall and extending longitudinally along the second base section slidably engages the base guide track 113 channel on the first base section 103. A first base guide rail is present on one side wall of the pair of opposing base side walls, and a second base guide rail is present on the other side wall of the second pair of opposing base side walls on the second base section. A first base guide track on one side wall of the pair of opposing base side walls on the first base section mates slidingly with the first base guide rail, and a second base guide track on the other side wall of the pair of opposing base side walls of the first base section mates slidingly with the second base guide rail.

Figure 15:
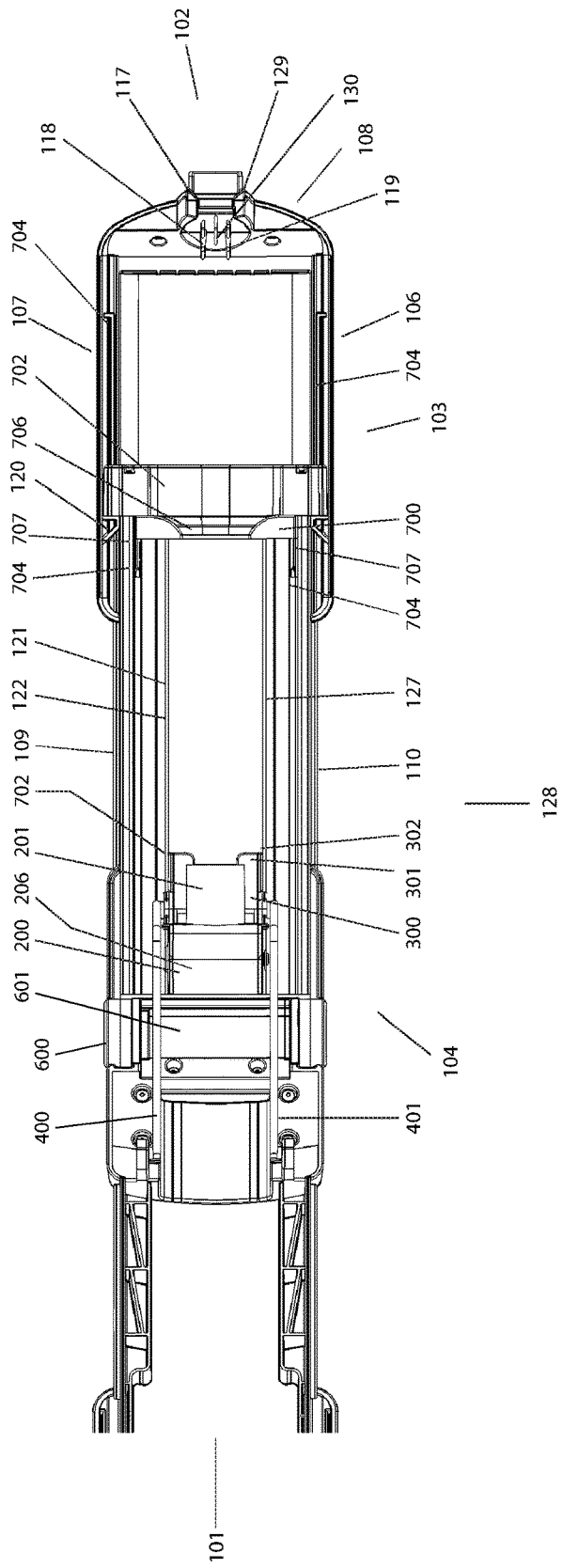
FIG. 15 is a top elevational view of the pump assembly of FIG. 14 in its open expanded state.
Figure 16:
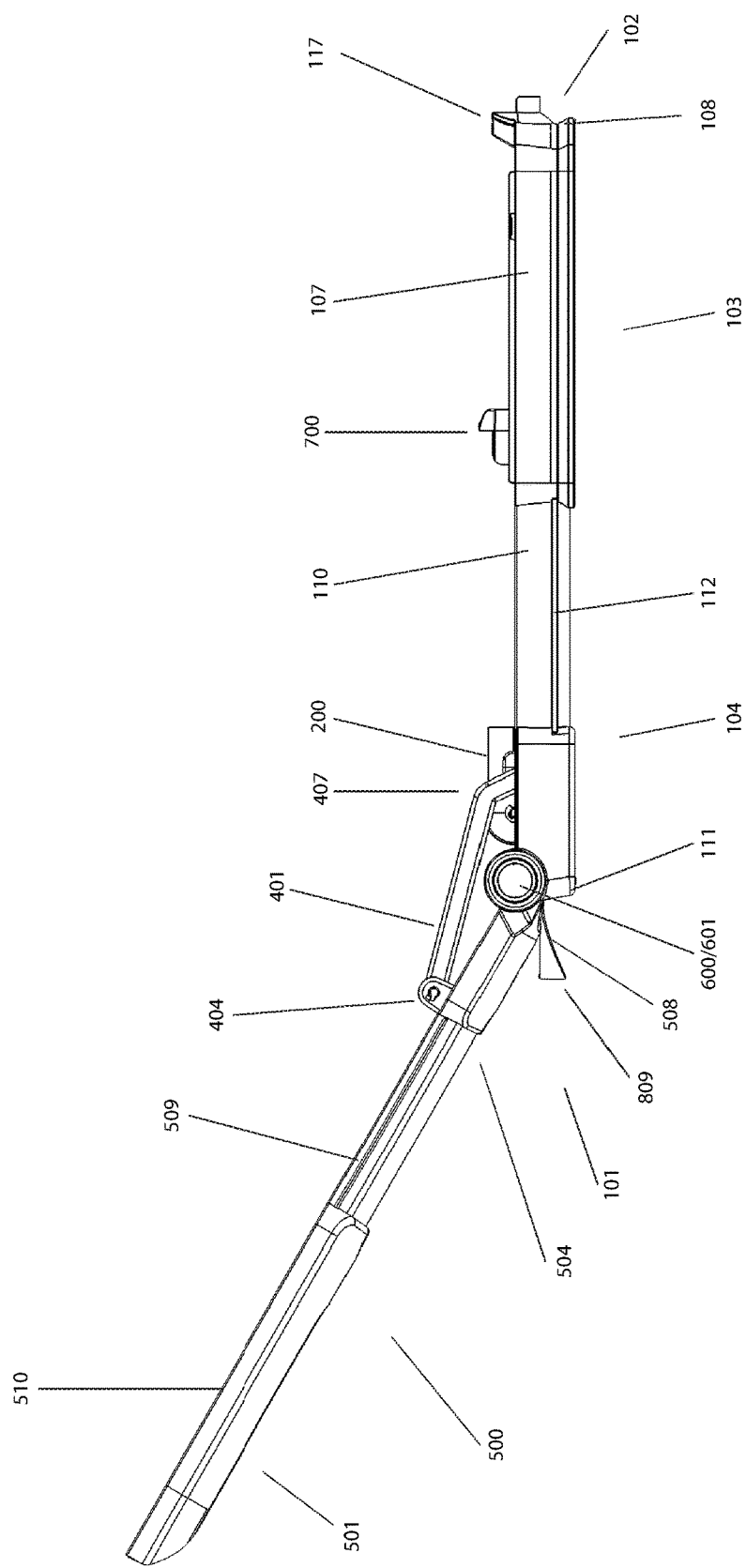
FIG. 16 is a side elevational view of the pump assembly of FIG. 14 in its open expanded state.
Figure 17:
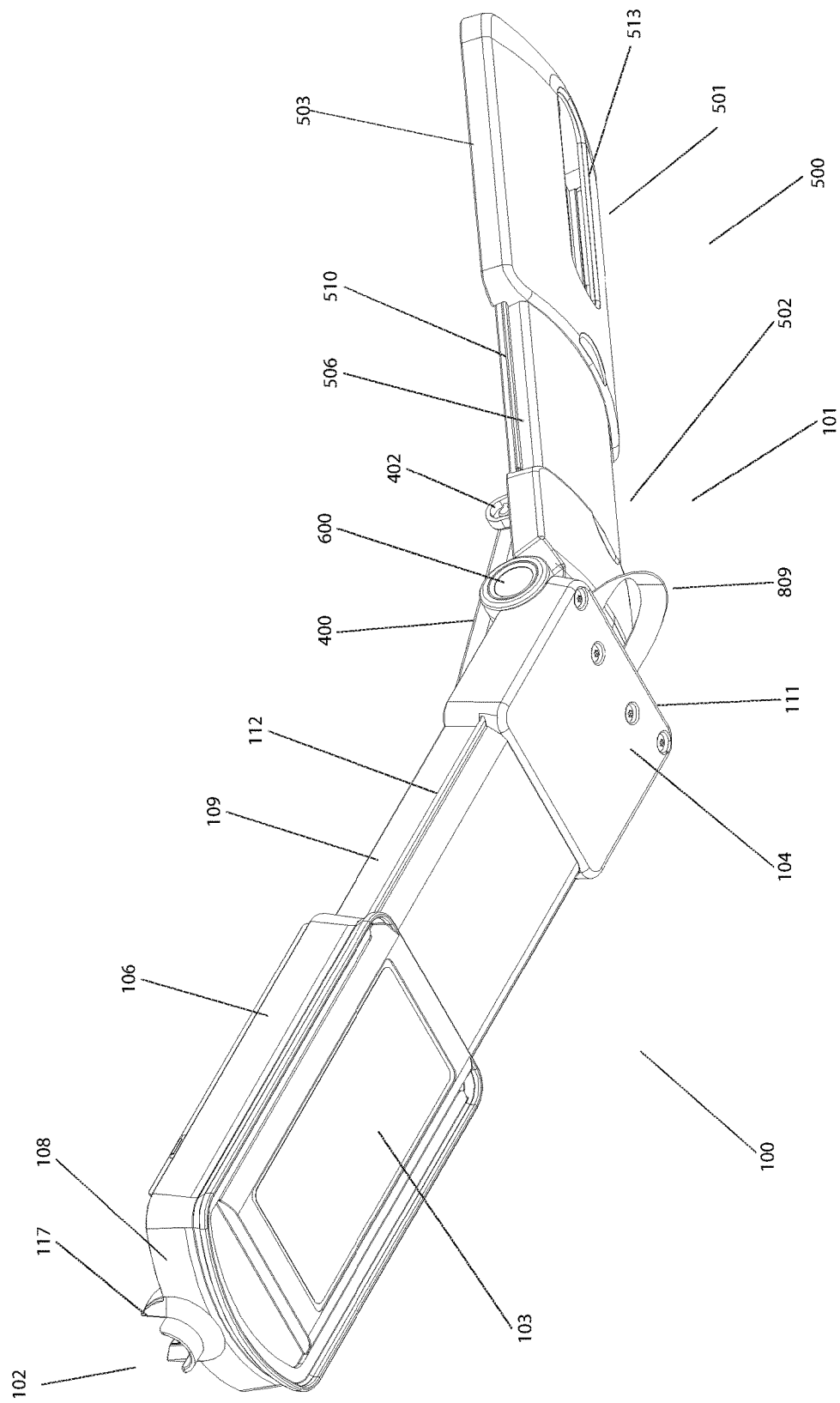
FIG. 17 is a bottom perspective view of the pump assembly of FIG. 14 in its open expanded state.
Figure 22:
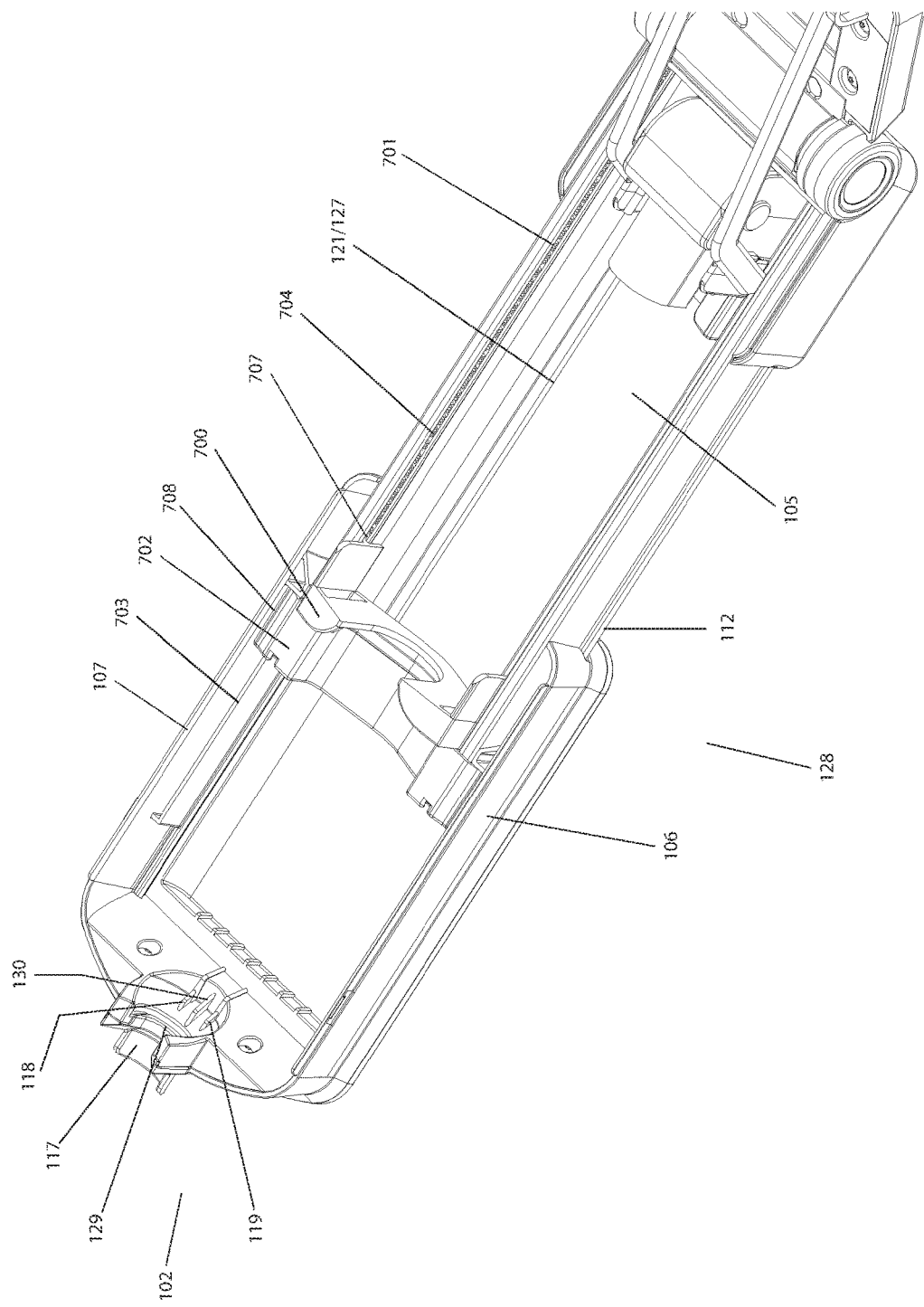
FIG. 22 is a perspective view of the pump assembly of FIG. 14 in its open expanded state depicting the distal end of the interior of the base.

As illustrated in FIGS. 14, 15 and 22, the distal wall 108 of the base has a luer locator 117 for receiving or locking the tip of a syringe onto the housing, in particular the luer locator is dimensioned to receive a luer type outlet of a syringe barrel. The luer locator 117 is in the form of an open collar dimensioned to receive a luer outlet of the syringe barrel. The distal wall can also have a partially circumferential flat surface 129 on the inside face of the distal wall, around the luer locator collar for contacting or receiving a disc luer connector, such as that described in International application no. PCT/US15/16929. The partially circumferential flat surface can be used to brace the disc luer connector when it is connected to a syringe and pressure applied on the plunger head. The distal wall also has rejector ramps 118, 119, and 130, which angle downward from the distal end to the proximal end, and is sufficiently spaced apart to allow seating of chamber bodies (e.g., syringe barrels) with defined diameters while rejecting non-fitting chamber bodies (e.g., syringe barrels). Different numbers and/or configurations of the rejection ramps can be used in a single pump assembly to cause rejection of syringe barrels having different shapes and sizes.

The cover 500 illustrated in FIGS. 14, 16, 17 and 23 includes a first cover section 501 and a second cover section 502, where the first cover section 501 and the second cover section 502 are in sliding engagement such that the first cover section 501 and the second cover section 502 are slidably movable relative to each other from a compacted position to an expanded position. The first cover section 501 includes a first pair of opposing cover section side walls 503 (front edge) and 504 (back edge), a first cover section distal wall 505, and an open end opposite the first cover section distal wall. The second cover section includes a second pair of opposing cover section side walls 506 (front edge) and 507 (back edge), a second cover section proximal wall 508, which can include the hinge 600, and an open end opposite the proximal wall. The cover can include a progress window 513 for viewing the chamber body seated in the base. In the embodiment shown, the progress window is present on the first cover section, towards the distal end of the housing. In certain embodiments, the second cover section at the open end opposite the proximal wall can have a notch matching the end shape of the progress window to increase the viewable area of the progress window when the pump is in the closed position. The embodiment of FIG. 14 also includes a detent element (not shown) configured as a beveled protrusion on the second cover section and a corresponding complementary hole which receives the beveled protrusion in the first cover section. The beveled shape allows the detent element to easily disengage from the hole when the first cover section and the second cover section are slidably moved to the compact position.

As illustrated in FIGS. 14, 18 and 19, the first cover section 501 and the second cover section 502 are in sliding engagement through a cover guide system, which includes a cover guide rail 509 on the second cover section slidably engaged to a cover guide track 510, which is a channel, on the first cover section. The cover guide rail 509 faces outward from the side wall, extending longitudinally along the second cover section and slidably engaged to the cover guide track 510 channel on the first cover section 103. A first cover guide rail is present on one side wall of the pair of opposing cover side walls, and a second cover guide rail is present on the other side wall of the second pair of opposing cover side walls on the second cover section. A first cover guide track on one side wall of the pair of opposing cover side walls on the first cover section mates slidingly with the first cover guide rail, and a second cover guide track on the other side wall of the pair of opposing cover side walls of the first cover section mates slidingly with the second cover guide rail.

Figure 23:
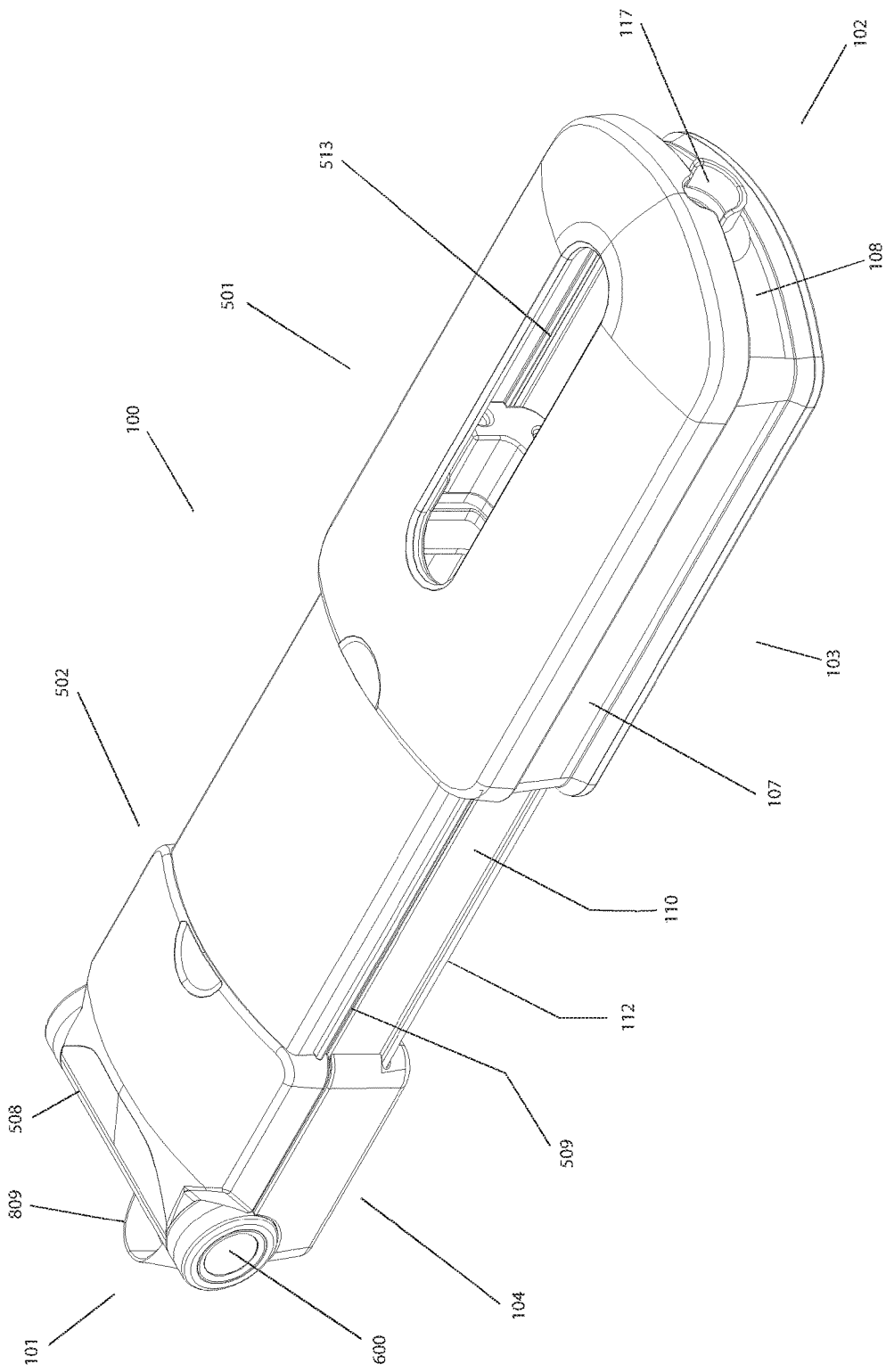
FIG. 23 is a perspective view depicting the pump assembly of FIG. 14 in its closed expanded state.
Figure 24:
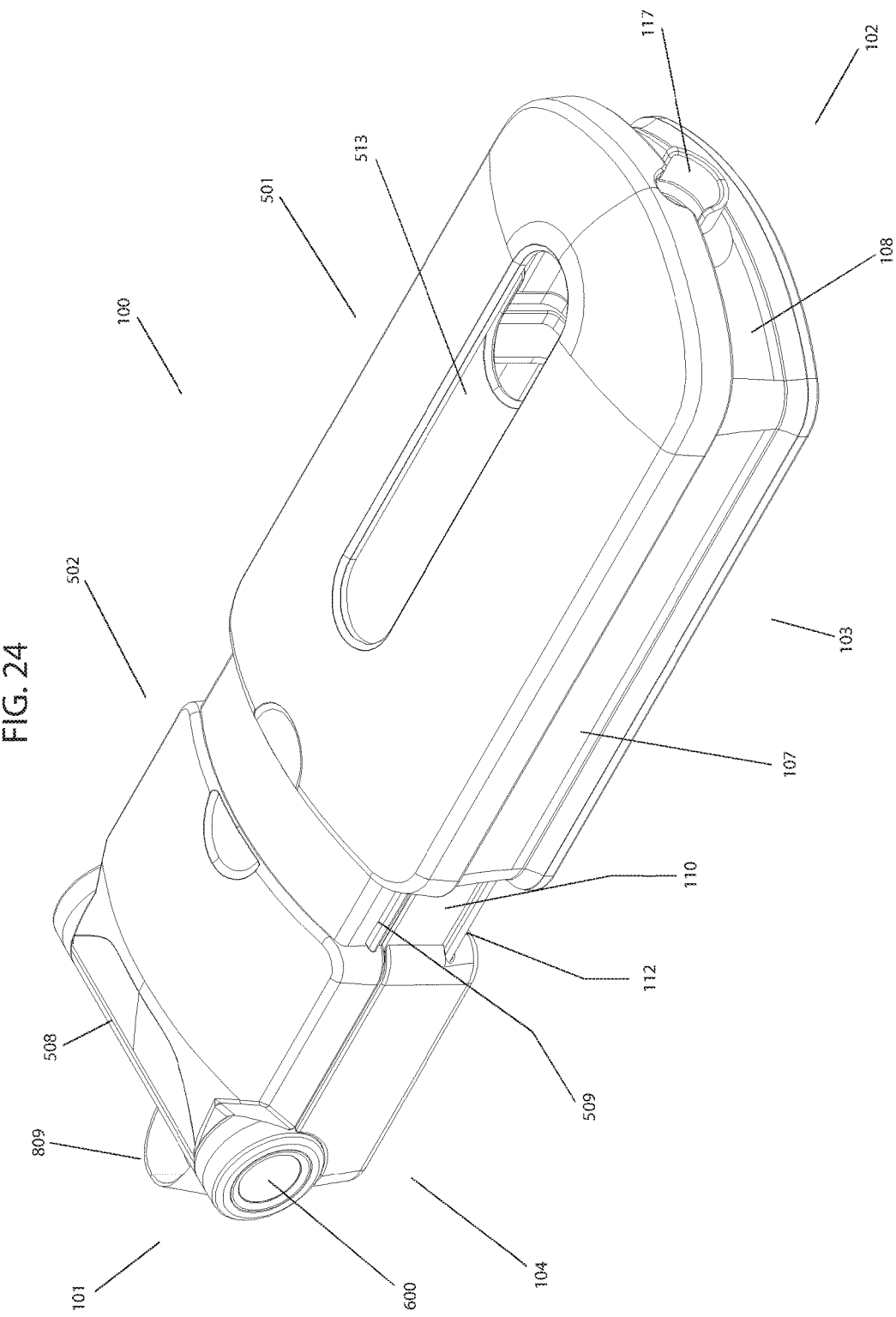
FIG. 24 is a perspective view of the pump assembly of FIG. 14 in its closed compacted state.
Figure 25:
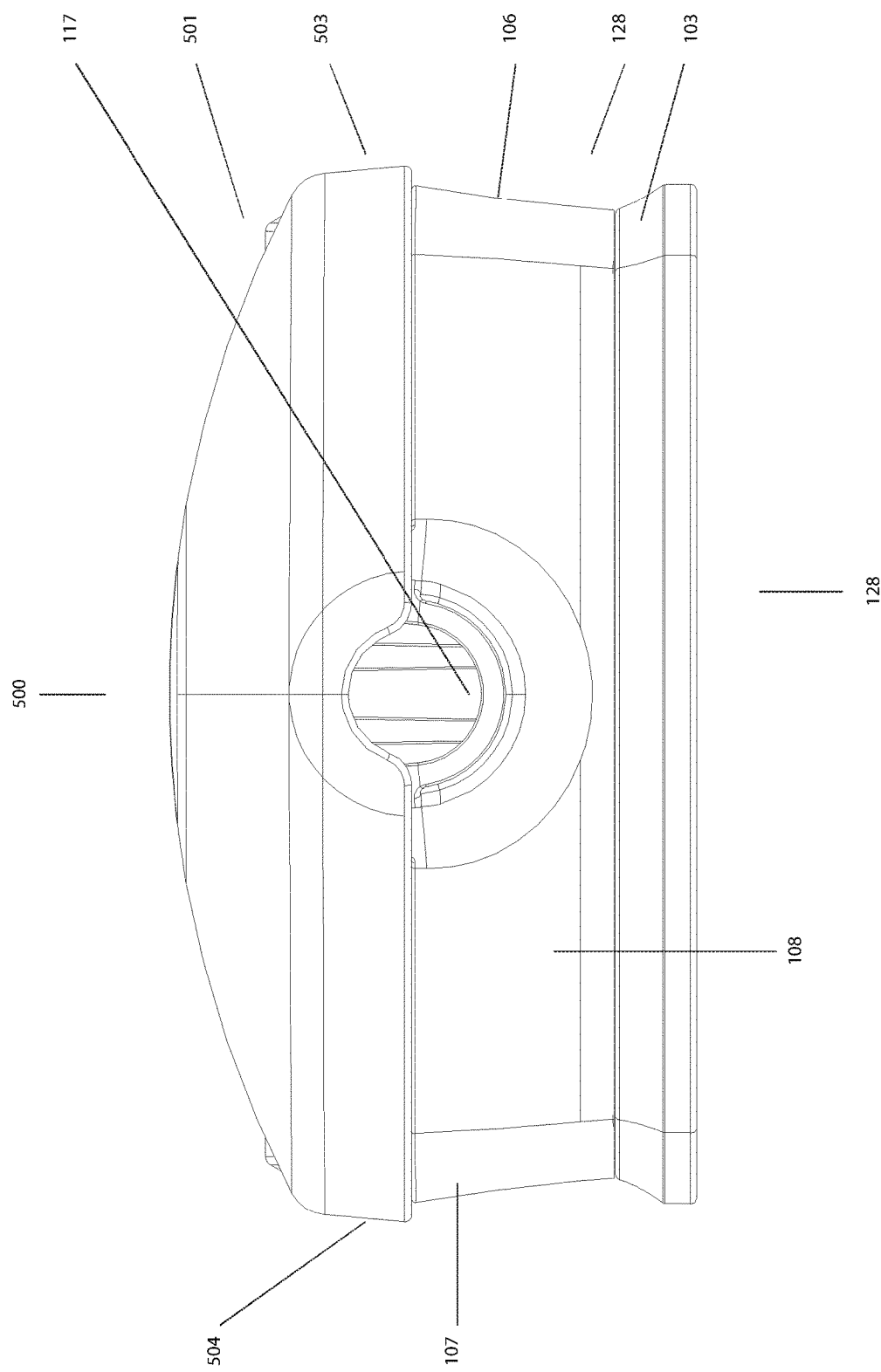
FIG. 25 is a view of the distal end of the pump assembly of FIG. 14.

The cover 500, as depicted in FIGS. 14 to 17, 23 and 24, is pivotally connected to the base 128 by a hinge 600, which has a damper 601. In the illustrated embodiment, the second base section 104 is pivotally connected to the second cover section 502 by the hinge 600 at the proximal end 101 of the second base section and the second cover section. The hinge 600 allows the cover to be raised or lowered, and the damper 601 dampens the opening of the cover, as discussed for the embodiment of FIG. 1, particularly when there is tension remaining in the spring when the cover is being opened. The hinge 600 connects the cover 500 to the base 128 such that slidably moving the second base section 104 relative to the first base section 103 moves together the second cover section 502 relative to the first cover section 501 when the cover is in the closed position. As discussed for the embodiment of FIG. 1, each of the cover 500 and the base 128 of the embodiment in FIG. 14 can expand or retract independently of the other when the pump is in the open state. FIG. 23 illustrates the pump assembly with the cover closed and the housing in the expanded position, while FIG. 24 illustrates the pump assembly with the cover closed and the housing in the compacted position.

Figure 21:
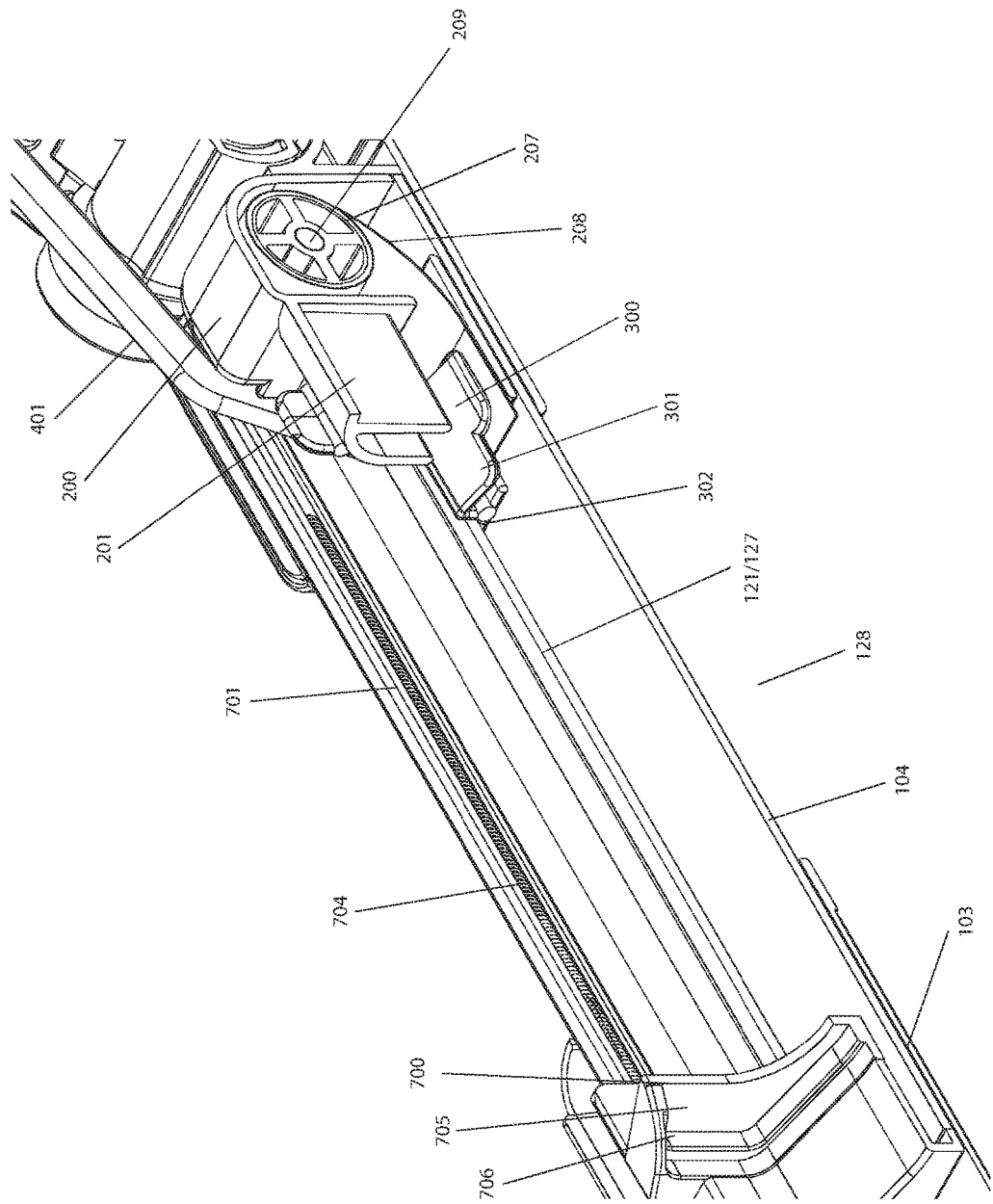
FIG. 21 is a perspective cross sectional view of the puller and pusher assembly with the spring housing, depicting the tape spring coiled around a spool in the pump assembly of FIG. 14.

The pump assembly further includes: a puller assembly 300, which in FIGS. 14, 15 and 21 is configured as a puller sled or plate 301 and is slidably engaged to the base 128; and a pusher assembly 200, which is slidably engaged to the base 128. In the embodiment, the puller 300 and the pusher 200 are slidably engaged to the second base section 104. A tape spring is connected 303 to the puller 300 at a first end portion of the spring, and connected to the puller 300 at a second end portion of the spring. In FIGS. 14 and 15, and as provided in more detail in FIG. 21, the pusher assembly includes a spring housing 206 and a spool 207, where a tape spring 208 is coiled around the spool. The tape spring can be directly attached to the spool, or the coil of tape spring allowed to sit on the spool without being directly attached to the spool. The spool 207 can be a spool drum mounted on a drum shaft 209. The pusher is dimensioned to contact the head of the plunger, which in FIG. 14, is a C shaped structure 201 having a recessed internal space, with supporting walls or ribs within the recessed space.

The puller 300 and the pusher 200 are in sliding engagement with the base 128. In FIGS. 14, 15, 18, 19, and 21, the pump assembly has a track system 121, which is comprised of a first track guide 122 on one side edge of the second base section 104 and a second track guide 127 on the other side edge of the second base section 104 (see, e.g., FIG. 18). In the embodiment shown, the first track guide 122 is a first channel facing inward and extending longitudinally along one inside side edge of the second base section, and the second track guide 127 is a parallel second channel facing inward and extending along the other inside side edge of the second base section such that the channels face each other. The puller 300 has puller guide elements 302, which are slidably engaged on the opposing first channel 122 and second channel 127. The pusher 200 has pusher guide elements 203 (see FIG. 19) which are slidably engaged on the opposing first channel 122 and the second channel 127. Since the same track system is used by the puller and the pusher, the puller 300 is slidably mounted on the track system, and thus positioned on the base, distal to the pusher 200.

As shown in FIG. 14, a first linkage 400 and a second linkage 401 pivotally couples the cover 500 to the puller 300, wherein the pivot points 402 and 403 of the first linkage 400 and the pivot points 404 and 405 of the second linkage 401 are positioned to slidingly move the puller towards the distal end when cover 500 is lowered and slidingly move the puller towards the proximal end when the cover 500 is raised. In particular, the pivot point 402 of the first linkage and the pivot point 404 of the second linkage are on the second cover section. The first linkage 400 and the second linkage 401 are bent at an angle, in particular at a defined angle, towards the puller 300. The point of the bend 406 and 407 on the linkage is offset from the center of the linkage and proximally to the puller to provide a bent linkage with two sections, where the first section is shorter than the second section of the linkage. In the embodiments shown, the first section, which is the shorter section, is pivotally connected to the puller 300 while the second section, the longer section, is pivotally connected to the second cover section 502. In certain embodiments, to keep the movement of the first linkage 400 and second linkage 401 coordinated for the movement of the puller 300, the first linkage 400 and the second linkage 401 are substantially the same length, have a bend position at substantially the same point on the linkage, and have substantially the same defined bend angle. In addition, for substantially parallel movement of the first linkage and the second linkage in moving the puller, the positions on the cover for the pivotal attachment of the first linkage and the second linkage are at substantially the same distance from the proximal end, and the distance from one side edge of the cover nearest the first linkage and the distance from the side edge of the cover nearest to the second linkage are also substantially the same.

Figure 20:
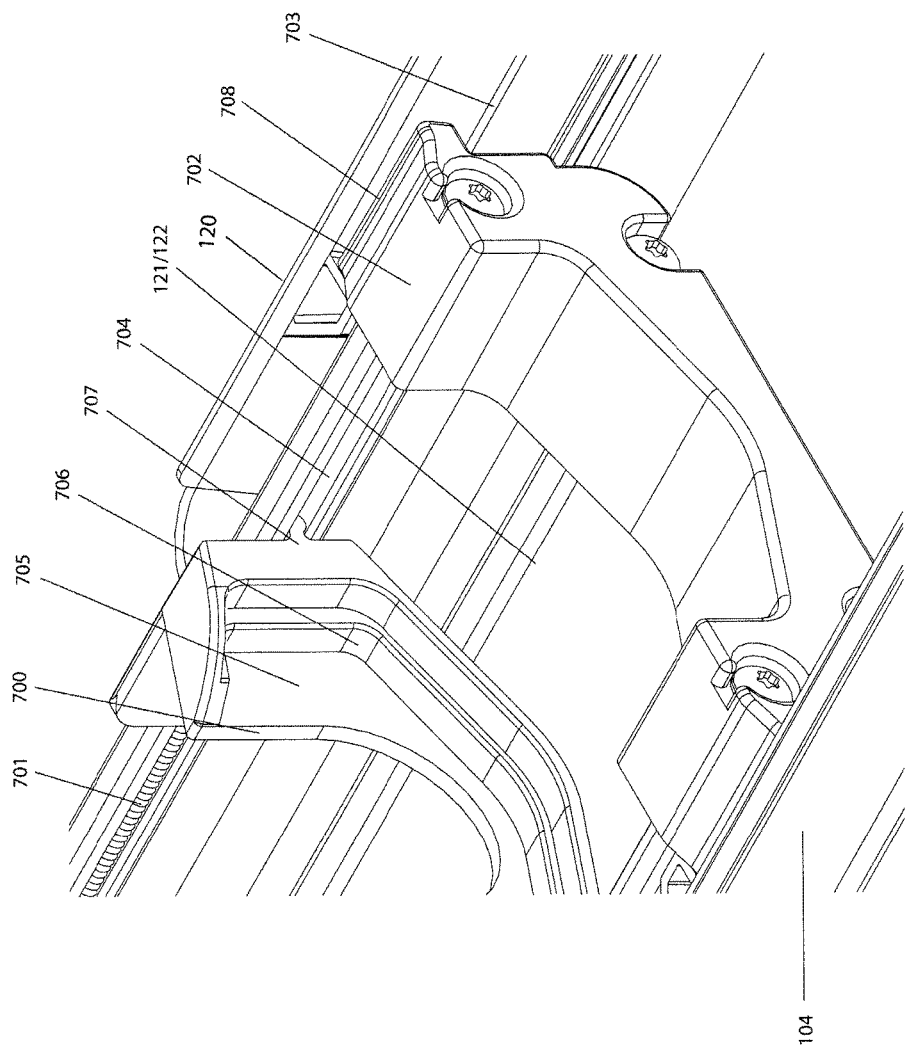
FIG. 20 is an enlarged perspective view of the collar with collar guide elements slidably engaged on a collar track system in the pump assembly of FIG. 14.

In the embodiment illustrated by FIGS. 14 and 15, the base 128 in the expanded position has a base interior 105 dimensioned to fit a chamber body having a plunger (e.g., syringe barrel having a syringe plunger), as described herein. The pump assembly 100 includes a collar 700 for centering and/or holding the chamber body. The collar 700 in the embodiment shown is an open collar and slidably engaged to the base through a collar guide track system 704, and can be moved proximally and distally. As shown in FIG. 20, the collar 700 has a seat (distal face) 705 and a recess 706 for receiving the end piece (e.g., finger flange) of the chamber body, and has collar guide elements 707 for slidably engaging the collar to the collar track system 704, where the collar track system comprises a second pair of parallel inward facing channels, e.g., a third channel and a fourth channel, wherein the third channel faces inward and extends longitudinally along the inside face of one side wall of the second pair of opposing side walls of the second base section, and the fourth channel faces inward and extends longitudinally along the inside face of the other side wall of the second pair of opposing side walls of the second base section, wherein the third channel and the fourth channel are parallel and face each other. The collar guide elements 707 are slidably engaged with the third channel and the fourth channels. As will be apparent to the skilled artisan, the third and fourth channels can also be formed between a flange which protrudes inward and extends longitudinally along the side wall of the pair of opposing side walls, and a guide rail which protrudes inward and extends longitudinally disposed below the flange, with a space in between the flange and the guide rail, where the collar guide elements slidably mount on the guide rail and engage the channel formed in between the flange and the guide rail. In certain embodiments, collar springs 701 are disposed within the collar track channels, e.g., third channel and fourth channel, and contact the collar on its proximal side. The collar springs 701 keep the collar 700 abutted or pressed against the collar stop or against the end piece of the plunger, but allow the collar to be moved proximally, for example when seating in the base a chamber body having a plunger. In certain embodiments, as shown in FIG. 20, the collar 700 can have more than one recess 706 nested in such a way to receive end pieces of differing sizes. For example, the collar can have a proximal recess and a distal recess, where the distal recess has a large face than the distal recess such that two differently sized end pieces can be accommodated by the collar. In certain embodiments, the collar has a plurality of nested recesses of different face sizes, wherein each recess receives an end piece of different size than the other recesses, wherein the face size of the recesses becomes smaller from the distal to the proximal end of the nested recesses.

In addition to the collar, the pump assembly as illustrated in FIGS. 14 and 20 includes a collar stop 702 for stopping the movement of the collar 700 distally at a defined position. In FIGS. 14 and 20, the collar stop 702 is attached to the open end of the second base section 104, where the collar stop is slidably engaged on a collar stop guide rail 703 through collar guide elements 708. When the pump assembly is in the closed state without a chamber body having a syringe seated in the housing, collar springs 701 push the collar 700 distally against the collar stop 702, wherein the collar stop prevent the collar from coming off the collar guide system 704. The collar stop 702 is also dimensioned to contact a base stop 120 (see, e.g., FIGS. 14 and 15) to prevent separation of the first base section 103 and the second base section 104 when the first base section and the second base are slidably moved relative to each other from the compacted position to the expanded position. The embodiment of FIG. 14 also includes a detent element (not shown) configured as a protrusion on the second base section and a corresponding complementary hole which receives the beveled protrusion in the first base section. The beveled shape allows the detent element to easily disengage from the hole when the first base section and the second base section are slidably moved to the compact position.

The operation of the pump assembly embodied in FIG. 14 is substantially the same as the operation of the pump assembly of FIG. 1. For operating the pump assembly of embodiment illustrated by FIGS. 14 to 25, the housing of the pump assembly 100 is expanded by slidably moving the first base section 103 and the second base section 104 relative to each other from the closed compacted position to the closed expanded position. A latch or lock holding the cover to the housing, when present, is released, and the cover 500 is raised away from the base, which slidably moves the puller 300 proximally as the linkages 403 and 404 pivotally coupling the cover 500 and the puller 300 move proximally with the raising of the cover. When the puller is sufficiently retracted towards the proximal end 101, a chamber body (e.g., syringe barrel) filled with a fluid and having a slidably disposed plunger is seated into the interior space 105 of the base 128 by slidingly moving the collar 700 proximally on the collar guide channels, and engaging the end piece (e.g., finger flanges) of the chamber body on the collar seat 705 and recessed space 706 complementary to the flanges. The collar springs disposed in the collar guide channels 701 keep the collar pressed against the end piece (i.e., finger flanges) of the syringe barrel. The outlet tip of the chamber body is placed on the luer locator 117 (see, e.g., FIG. 14). In a typical infusion set up, a tubing or another connector is attached to the outlet of the chamber body. To apply force to the head of the plunger, the cover 500 is lowered, which moves the linkages 403 and 404 distally, thereby slidably moving the puller 300 towards the distal end of the base. Movement of the puller distally also moves the pusher until the pusher head contacting portion 201 contacts the head of the syringe plunger and presses on the plunger head. The resistance of the plunger results in unwinding of the tape spring from the coiled tape spring in the spring housing of the pusher as the puller is moved further distally when the cover is closed. The uncoiled tape spring provides substantially constant force on the pusher and thus constant force on the plunger head, thereby resulting in expelling of the contents in the chamber of the chamber body as the plunger is forced to move distally. Once the contents of the chamber has been ejected and the plunger displaced distally, the cover is opened and raised, which retracts the puller proximally, disengaging the pusher from contacting the head of the plunger, and allowing the chamber body having the plunger to be removed. The cover is then closed, and the housing placed in the compacted position, as illustrated in FIG. 24, by pushing the second base section and first base section towards each other.

As discussed herein, the pump assembly 100 may be used to administer liquids and preferably therapeutic liquids. In certain embodiments, the pump is used for subcutaneous or intravenous administration of therapies to a patient in need. For example, the pump may be used to administer antibiotics, chelating agents or biologic therapies such as immune globulin therapy to a patient in need.

In certain embodiments, the spring 208 of the pump is selected to properly correspond with the viscosity of the therapy. For example, for a low viscosity liquid, the spring 208 of the pump may be selected from a spring with less tension in order to exert less force on the head of the plunger 806. For a high viscosity fluid, such as immune globulin, a higher tension spring may be used in order to exert more force on the head of the plunger 806.

In certain embodiments, the tubing attached to the syringe can be selected to control the flow rate of the liquid. For example, tubing with a narrow internal diameter may be selected when a slower rate of administration is desired while a tubing with a wider internal diameter may be selected for a more rapid administration. In addition, the tubing may be oriented in a series or parallel configuration in order control the rate of administration to the patient as in PCT/US2014/016426, incorporated by reference in its entirety.

The disclosure also provides methods of using the pump for administering liquids. In certain embodiments, any of the pumps described herein may be used to administer a liquid such as a therapeutic agent. In certain embodiments, the base of the pump is expanded from its compacted state. A syringe pre-loaded with a liquid is loaded into the base of the pump as described herein. The pre-loaded syringe can be adapted with tubing and needles for infusion therapy. A patient or a third party can position the one or more needles attached to the tubing in the body of the patient. Once the syringe is situated in the base of the pump with tubing extending from the housing, a cover may be lowered to begin administration of the liquid. The cover can be opened during the administration of the liquid to stop the administration. Once the administration is complete, the user can open the cover and remove the syringe. The pump can be compacted for storage or portability.

In another aspect, the pump assembly is used with a syringe in an infusion system for administering a therapeutic fluid, such as an antibiotic, immunoglobulin preparations or other therapeutic antibodies; or chemotherapeutic agents. In various embodiments, the infusion system or related kits can comprise a pump assembly described herein. In other embodiments, the infusion system or related kits can include in addition to the pump assembly, one or more of: a syringe dimensioned to seat in the pump assembly; a luer connector or disc luer connector for connecting the syringe to components of the infusion system; a tubing set, in particular an infusion tubing set, such as for connecting a injection needle to the syringe; a flow controller for controlling the flow of therapeutic fluid for administration; and an injection needle set for administering the therapeutic fluid into a patient's body. Various infusion systems with different combinations of the foregoing components can be made.

While specific embodiments of the subject invention have been discussed, the above specification is illustrative and not restrictive. Many variations of the invention will become apparent to those skilled in the art upon review of this specification.

What is claimed is:

1. A pump enclosure assembly comprising:
an expandable base having a proximal end and a distal end, the base comprising: a first base section and a second base section, wherein the first base section is in sliding engagement with the second base section such that the first base section and the second base section are slidably movable relative to each other between a compacted position and an expanded position, wherein the base in the expanded position is adapted to seat a chamber body having a plunger, wherein the chamber body defines a bore and an outlet, and the plunger is slidably disposed within the bore;
a pusher in sliding engagement with the base, wherein the pusher is dimensioned to contact the head of the plunger;
a puller in sliding engagement with the base;
a spring comprising a first end portion and a second end portion, wherein the first end portion is connected to the puller and the second end portion is connected to the pusher, whereby slidably moving the puller distally when the chamber body having the plunger is seated in the base causes the pusher to contact and exert force on the head of the plunger; and an expandable cover pivotally connected to the proximal end of the base, a linkage pivotally coupled between the cover and the puller and structured and arranged to translate the opening of the cover to the movement of the puller and pusher towards the proximal end, and the closing of the cover when the chamber body has been disposed engages the pusher against the plunger and moves the puller towards the distal end and tensions the spring;

wherein the expandable base and expandable cover enclose the chamber body, the spring, puller, and pusher structured and arranged to provide force to the plunger of the chamber body providing a pressure pump.

2. The pump assembly of claim 1, wherein the chamber body comprises a syringe barrel and the plunger is a syringe plunger.

3. The pump assembly of claim 1, wherein the pressure pump operates in equilibrium based on back pressure and flow rate.

4. A pump enclosure assembly, comprising:
a housing having a distal end and a proximal end, the housing comprising:
  (a) an expandable base comprising a first base section and a second base section, wherein the first base section is in sliding engagement with the second base section such that the first base section and the second base section are slidably movable relative to each other between a compacted position and an expanded position, wherein the base in the expanded position is adapted to seat a chamber body having a plunger, wherein the chamber body defines a bore and an outlet, and the plunger is slidably disposed within the bore;
  (b) an expandable cover comprising a first cover section and a second cover section, wherein the first cover section is in sliding engagement with the second cover section, and wherein the cover is pivotally connected to the base at a position allowing the cover to open and close, and such that slidably moving the second base section relative to the first base section moves together the second cover section relative to the first cover section when the cover is in the closed position;
a pusher in sliding engagement with the base, wherein the pusher is dimensioned to contact the head of the plunger;
a puller in sliding engagement with the base;
a spring comprising a first end portion and a second end portion, wherein the first end portion is connected to the puller and the second end portion is connected to the pusher; and
a first linkage pivotally coupled to the cover and the puller, wherein the pivots of the first linkage are located to move the puller towards the distal end when the cover is lowered and move the puller towards the proximal end when the cover is raised,
whereby moving the puller towards the distal end by lowering the cover when the chamber body having the plunger is seated in the base causes the pusher to contact and exert force on the head of the plunger, the spring, puller, and pusher structured and arranged to providing force to the plunger of the chamber body providing a pressure pump.

5. The pump assembly of claim 4, wherein the chamber body comprises a syringe barrel and the plunger is a syringe plunger.

6. The pump assembly of claim 4, wherein the cover is dimensioned to cover the base in the compacted and expanded positions.

7. The pump assembly of claim 4, wherein the first linkage is rigid.

8. The pump assembly of claim 4, further comprising a second linkage pivotally coupling the cover to the puller, wherein the pivots of the second linkage are located such that the second linkage together with the first linkage pushes the puller towards the distal end when the cover is lowered, and the second linkage together with the first linkage pulls the puller towards the proximal end when the cover is raised.

9. The pump assembly of claim 8, wherein the second linkage is rigid.

10. The pump assembly of claim 4, comprising a base guide system disposed on the first base section or the second base section for guiding the first base section and second base section slidably movably between the compacted position and the expanded position.

11. The pump assembly of claim 10, wherein the base guide system comprises a base guide rail on the first base section or the second base section, and a corresponding complementary base guide track on the second base section or the first base section, wherein the base guide rail mates slidably with the corresponding complementary base guide track.

12. The pump assembly of claim 4, further comprising a base stop on the first base section or the second base section for preventing the first base section and the second base section from separating when the first base section and the second base section are in the expanded position.

13. The pump assembly of claim 4, comprising a cover guide system disposed on the first cover section or the second cover section for guiding the first cover section and the second cover section slidably movably between the compacted position and the expanded position.

14. The pump assembly of claim 13, wherein the cover guide system comprises a cover guide rail on the first cover section or the second cover section and a corresponding complementary cover guide track on the second cover section or the first cover section, wherein the cover guide rail mates slidably into the corresponding complementary cover guide track.

15. The pump assembly of claim 4, further comprising a cover stop on the first cover section or second cover section for preventing the first cover section and the second cover section from separating when the first cover section and the second cover section are in the expanded position.

16. The pump assembly of claim 4, further comprising a collar for centering and/or holding the chamber body, wherein the collar is positioned distal to the pusher.

17. The pump assembly of claim 16, further comprising a collar stop for preventing movement of the collar distally at a defined position.

18. The pump assembly of claim 17, wherein the collar stop is attached to the distal end of the second base section.

19. The pump assembly of claim 4, comprising one or more track systems on the base for slidably mounting the puller, the pusher, and/or the collar.

20. The puller assembly of claim 19, wherein the track system is present on the second base section.

21. The pump assembly of claim 19, wherein the puller comprises a puller guide element which slidably mounts the puller to the one or more track systems.

22. The pump assembly of claim 19, wherein the pusher comprises a pusher guide element which slidably mounts the pusher to the one or more track systems.

23. The pump assembly of claim 19, wherein the collar comprises a collar guide element which slidably mounts the collar to the one or more track systems.

24. The pump assembly of claim 4, wherein the spring comprises a tape spring.

25. The pump assembly of claim 24, wherein the tape spring produces substantially constant force on the plunger head of a chamber body seated in the base when the puller is slidably moved towards the distal end.

26. The pump assembly of claim 4, wherein the cover is pivotally connected to the proximal end of the base by a hinge.

27. The pump assembly of claim 26, further comprising a damper to dampen the opening motion of the cover.

28. The pump assembly of claim 4, further comprising a latch assembly or lock assembly for keeping the cover in the closed position on the base.

29. The pump assembly of claim 4, further comprising a luer locator on the distal end of the first base section for holding or locking the outlet of the chamber body.

30. The pump assembly of claim 4, further comprising a rejector for rejecting a non-fitting chamber body seated in the base.

31. The pump assembly of claim 4, wherein the cover comprises a progress window for viewing the chamber body when the cover is closed.

* * * * *